US005595182A

United States Patent [19]
Krivitski

[11] Patent Number: 5,595,182
[45] Date of Patent: *Jan. 21, 1997

[54] CARDIOVASCULAR MEASUREMENTS BY SOUND VELOCITY DILUTION

[75] Inventor: Nikolai M. Krivitski, Ithaca, N.Y.

[73] Assignee: Transonic Systems, Inc., Ithaca, N.Y.

[*] Notice: The term of this patent shall not extend beyond the expiration date of Pat. No. 5,453,576.

[21] Appl. No.: 485,790

[22] Filed: Jun. 7, 1995

Related U.S. Application Data

[62] Division of Ser. No. 327,984, Oct. 24, 1994, Pat. No. 5,453,576.

[51] Int. Cl.$^6$ ........................................... A61B 8/00
[52] U.S. Cl. ..................... 128/692; 128/661.08
[58] Field of Search ............. 128/660.01, 660.02, 128/661.07, 661.08, 661.1, 672, 691, 698, 747, 692, 662.06; 73/40, 40.5 R, 40.5 A, 596, 597, 754, 861.25; 356/28, 28.5; 424/9.52

[56] References Cited

U.S. PATENT DOCUMENTS

| | | |
|---|---|---|
| 3,640,271 | 2/1972 | Horton . |
| 3,964,479 | 6/1976 | Boag et al. . |
| 4,142,796 | 3/1979 | Riva ............................................. 356/28 |
| 4,316,391 | 2/1982 | Tickner ................................. 73/861.25 |
| 4,353,368 | 10/1982 | Slovak et al. . |
| 4,391,124 | 7/1983 | Drost et al. . |
| 4,432,231 | 2/1984 | Napp et al. . |
| 4,434,648 | 3/1984 | Drost et al. . |
| 4,777,958 | 10/1988 | Ophir . |
| 4,797,655 | 1/1989 | Orndal et al. . |
| 4,856,321 | 8/1989 | Smalling et al. . |
| 5,038,789 | 8/1991 | Frazin ................................. 128/662.06 |
| 5,121,749 | 6/1992 | Nassi et al. ........................ 128/662.06 |
| 5,230,341 | 7/1993 | Polaschegg . |
| 5,312,550 | 5/1994 | Hester . |

OTHER PUBLICATIONS

C. Aldridge, et al, "The Assessment of Arteriovenous Fistulae Created for Hemdialysis from Pressure and Thermal Dilution Measurements, Journal of Medical Engineering & Technology", vol. 8 No. 3 (May/Jun.) pp. 118–124.

Serial blood water estimations and in–line blood viscometry: the continuous measurement of blood volume during dialysis procedures, R. N. Greenwood, C. Aldridge, and W. R. Cattell, Clinical Science (1984) 66. 575–583.

The Velocity of Ultrasound in Human Blood Under Varying Physiologic Parameters, E. L. Bradley, III, and Jose Sacerio, Journal of Surgical Research, vol. 12 No. 4, pp. 290–297.

Tissue Charactrerization with Ultrasound, vol. II Results and Applications, James F. Greenleaf, Ph.D.

(List continued on next page.)

*Primary Examiner*—George Manuel
*Attorney, Agent, or Firm*—Jones, Tullar & Cooper, P.C.

[57] ABSTRACT

An apparatus and method for measuring hemodynamic parameters includes a sound velocity sensor coupled to at least one of an arterial or venous portion of a blood system. An indicator medium is injected into the blood system upstream of the sensor to dilute the bloodstream, and the sensor detects the dilution through changes in measured sound velocity. The changes are recorded and used to determine hemodynamic parameters.

49 Claims, 16 Drawing Sheets

OTHER PUBLICATIONS

A new method of Continuous Hemoglobinometric Measurement of Blood Volume During Hemodialysis, U. Schallenberg, S. Stiller & H. Mann, Life Support Systems (1987), 5, 293–305.

On–Line Measurement of Blood Water Concentration in the Extracorporeal Circulation of Hemodialysis Patients, Daniel Schneditz, Allen M. Kaufman and Nathan W. Levin, Annual International Conference of the IEEE Engineering in Medicine and Biology Society, vol. 13, No. 4, 1991.

A Dye–Dilution Method for the Determination of Blood Flow in Cimino–Brescia Arteriovenous Fistulae, Jan Gothlin, Eric Lindstedt, and Tord Olin, Investigative Urology, vol. 15 No. 2, 1977.

The Assessment of Arteriovenous Fistulae Created for Haemodialysis from Pressure and Thermal Dilution Measurements, C. Aldridge, R. N. Greenwood, W. R. Cattell, Journal of Medical Engineering and Technology, vol. 8, No. 3 (May/Jun.).

Cardiopulmonary Recirculation in Dialysis, Daniel Schneditz, et al, ASAIO Journal 1992.

Journal Article, Med Tekh 1987 Jan.–Feb.; (1):6–9, Krivitskii, Kislukhin, (Russian Abstract) Determination of the volume of extravascular fluid in the lungs by blood electrical resistance using a dilution method.

Assessment of Arteriovenous Fistulae from Pressure and Thermal Dilution Studies: Clinical Experience in Forearm Fistulae; Clinical Nephrology. vol. 23, No. 4 1985 (pp. 189–197).

A Sound–Speed Sensor for the Measurement of Total Protein Concentration in Disposable, Blood–Perfused Tubes. J. Acoust, Soc. Am. 8 (6), Dec. 1989.

The Assessment of Arteriovenous Fistulae Created for Haemodialysis from Pressure and Thermal Dilution Measurements. Journal of Medical Engineering & Technology, vol. 8, No. 3 (May/Jun.), pp. 118–124.

Speed of Sound in Sea–Water Samples, The Journal of the Acoustcal Society of America, vol. 52 No. 3 (Part 2) 1972.

Brochure Transonic Systems Inc., 1993 New Products Catalog, pp. 1–24.

"Cardiopulmonary Recirculation in Dialysis," Daniel Schneditz et al, ASAIO Journal 1992, pp. 194–196.

"On–Line Measurement of Blood Water Concentration in the Extracorporeal Circulation of Hemodialysis Patients" Daniel Schneditz et al, Annual Conference of the IEEE Engineering in Medicine and Biology Society, vol. 13, No. 4, 1991 pp. 1651–1652.

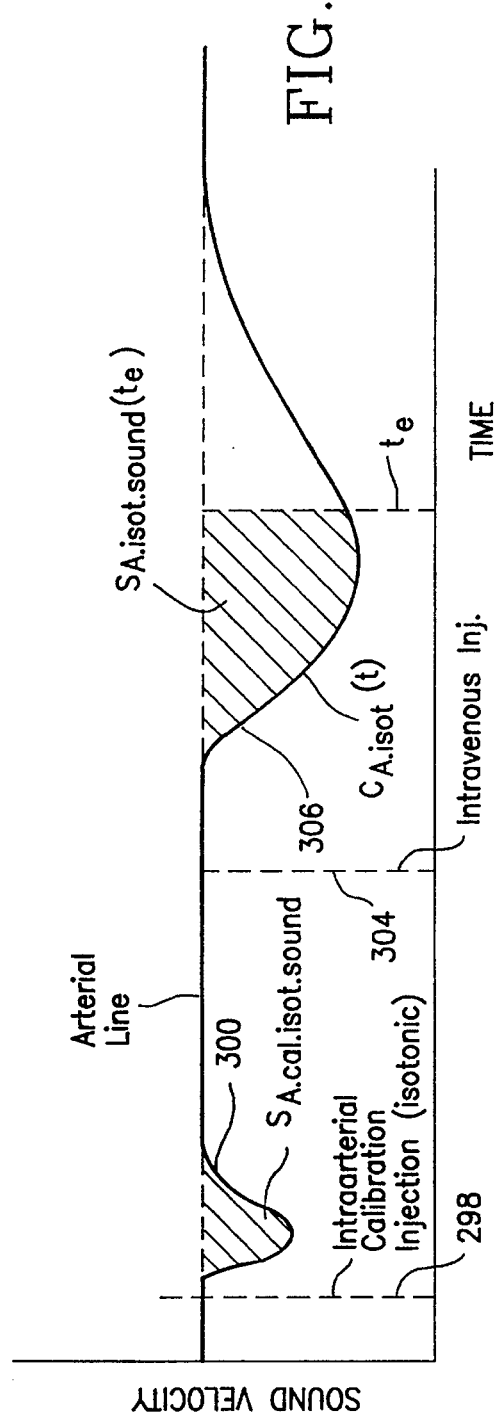
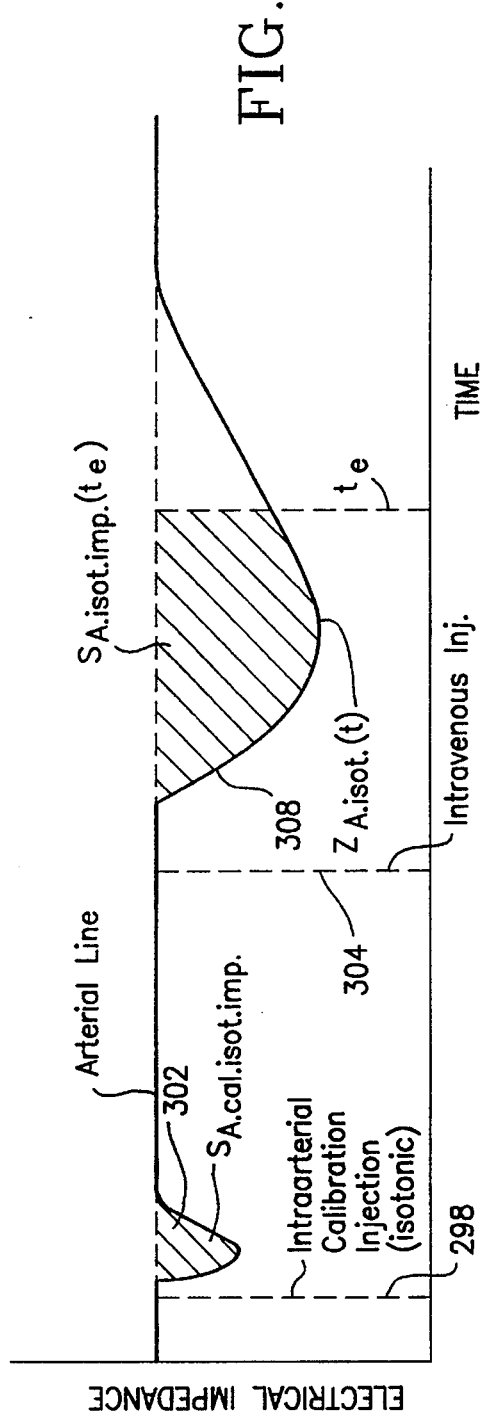

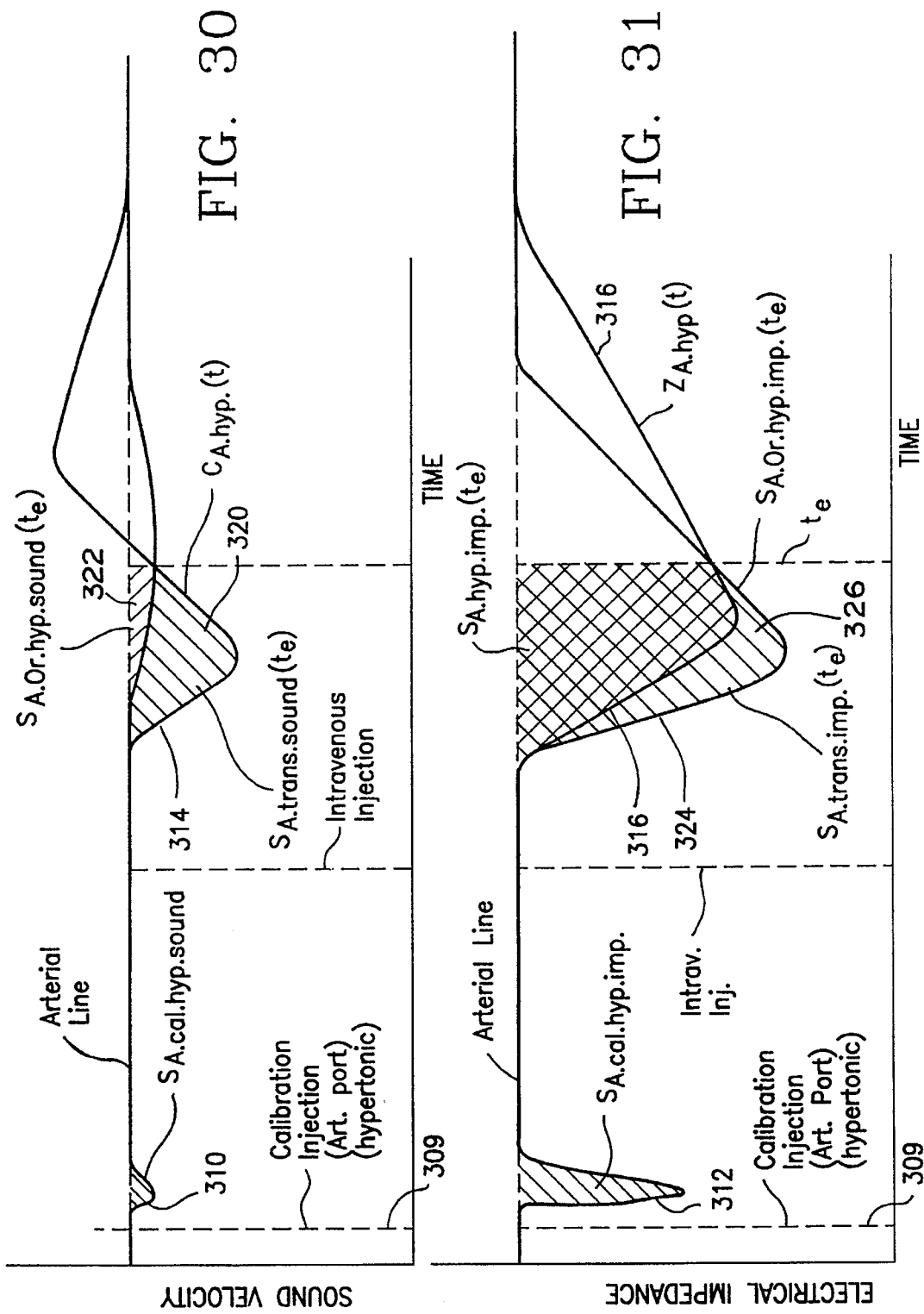

1

CARDIOVASCULAR MEASUREMENTS BY SOUND VELOCITY DILUTION

This is a divisional of application(s) Ser. No. 08/327,984 filed on Oct. 24, 1994, now U.S. Pat. No. 5,453,576.

BACKGROUND OF THE INVENTION

The present invention relates, in general, to the measurement of hemodynamic parameters by indicator dilution, and more particularly to measurements of blood flow, blood volume, cardiac output, protein concentration, lung water, and solution clearance through the measurement of the sound velocity dilution effects of an indicator in the bloodstream of a patient.

In a large number of medical procedures, it is very important to monitor with precision hemodynamic parameters in a patient. For example, in procedures such as hemodialysis, a filter is used to remove selected particles and liquids from the patient's bloodstream, but if this material is removed too quickly, the vascular system of the patient may collapse.

Medical parameters such as protein concentration in the blood, cardiac output, lung water content, blood circulating volume, and the like also require careful measurement and monitoring, and improved accuracy in such measurements is highly desirable.

Difficulties in making such measurements have resulted from the fact that such procedures usually involve extracorporeal circulation of the blood from a patient through, for example a blood treatment system, and in many cases the effects of the system itself on the blood flow or on the measurement devices is unknown. For example, if blood is directed to a dialysis filter through plastic tubing, the effect of the plastic material on measuring equipment using ultrasound waves may not be known with any certainty, since the characteristics of the material can vary from one tube to another. Difficulties are also encountered in perivascular measurements, i.e., measurements made using sensors mounted on a blood vessel, for the thickness of a vessel wall can adversely affect the measurement. Even when measurements are being made in the patient's body, as by an ultrasonic blood flow meter clamped around a blood vessel, the thickness and morphology of the vein/artery will affect the measurement.

SUMMARY OF THE INVENTION

It is, therefore, an object of the present invention to provide a method and apparatus for accurately and reliably measuring blood parameters in situ within a patient's vein or artery, externally of the vein or artery, or in tubing leading to a blood treatment system which carries the blood exteriorly of the patient's body.

It is another object of the invention to accurately and reliably measure a patient's blood to determine blood parameters such as blood volume changes, protein concentration or cardiac output, to determine lung water, and to determine solution clearance of a blood testing or monitoring system, through measurement, over a period of time, of blood dilution.

It is another object of the present invention to measure parameters of a patient's blood by measuring sound velocity dilution in the blood resulting from the injection of known quantities of a diluting indicator material.

Briefly, the present invention relates to a method and apparatus for measuring blood parameters by dilution. More specifically, the invention relates to a method and apparatus for measuring various blood parameters utilizing a dilution process wherein an indicator material such as a saline solution is injected into a bloodstream and its downstream effects on measured quantities such as the velocity of ultrasound in the bloodstream and electrical impedance of the blood provide information about a variety of blood flow parameters.

It is known that the velocity of ultrasound in blood is a function of, among other things, the proteins and ions contained in the blood, with the sound velocity increasing with an increase in protein concentration. Accordingly, the velocity of sound through a blood sample can be varied by diluting the blood with an indicator material having different acoustical characteristics than those of the blood; for example, through the use of a saline solution that has no proteins. By injecting a known volume of such an indicator into a known blood flow, the diluting effect of the indicator over a period of time can be accurately determined by a sensor responsive to changes of sound velocity in the blood. The sensor is positioned downstream of the injection so that the indicator passes the sensor, with the measured diluting effect being used to determine various blood parameters.

The measurements can be made in situ in a patient's vessel through the use of a catheter to provide intravascular measurements, or can be done through the use of measuring sensors clamped onto a patient's blood vessel, to provide perivascular measurements. In another alternative, the measurements may be made in an extracorporeal blood system in which clamp-on measuring sensors are secured; for example, to tubing leading to exterior blood treatment equipment such as a hemodialysis machine, or the like. In general, then, in accordance with the present invention, ultrasound measurements are made of the characteristics of a patient's blood. Thereafter, a bolus, or known volume, of an indicator material having different characteristics than those of the blood is injected into the bloodstream and measurements are made of changes in sound velocity to determine the passage of the bolus past the sensor. The changes in such characteristics can then be plotted and used to determine parameters such as blood flow, blood volume, cardiac output, protein concentration, lung water, solution clearance, blood recirculation within a treatment system, and the like. Dilution measurements are principally by sound velocity, with increased accuracy being provided by measuring both sound velocity and amplitude. Additional sensors can be used to measure various other blood characteristics such as temperature or electrical impedance to increase the accuracy of the determinations made by the present invention.

More particularly, the blood parameter measurements in accordance with one embodiment of the present invention can be carried out by injecting a known volume of an indicator isotonic saline solution at blood temperature through a catheter into an artery, for example, or into an arterial tube in a blood treatment system. This solution, which is carried downstream by the arterial blood flow, dilutes the blood protein concentration, thereby producing a change in the measured velocity of sound in the blood when it passes through an arterial sensor located downstream from the injection point. This change in sound velocity permits a rapid and accurate intravascular measurement of, for example, cardiac output (volume per unit time), as well as measurement of blood protein concentration.

In cases where the sensor does not make direct contact with the blood, as in perivascular or clamp-on applications, the ultrasonic wave of the sensor passes through a vessel or tube as well as through the blood. The measured sound velocity then is a function of the material and the geometry of the vessel or tube and their acoustical properties, as well as of the acoustical properties of the blood. In such cases, the effects of the vessel or tube must be determined and then canceled out of later measurements so that the results of later blood parameter measurements will be independent of the sonic and geometric properties of the tube or the artery/vein.

Sound velocity is also a function of blood temperature, and accordingly in another embodiment of the invention the indicator may be a volume of a liquid having a different temperature than that of the bloodstream. In this case, the indicator material can be detected not only by a sound velocity sensor, but by a temperature sensor, as well, to provide improved accuracy. In similar manner, indicators having a different optical density or electrical impedance than that of the bloodstream may be used, with appropriate sensors, to detect changes in blood characteristics.

The intravascular sensors described above can be located in either an artery or a vein of a patient, or both. When in an artery, including the pulmonary artery, measurements of cardiac output (CO) may be made, but when in a vein, the measurement is of the flow through the patient's organs. In the latter case, the measurements can be used to determine solution clearance; that is, the ability of an organ to respond to, or to recover, different solutes. Thus, for example, a special solution can be injected into an artery upstream of an organ to be tested and measurements made in a vein downstream of the organ to measure the organ's reaction to that solution and from this to determine specific characteristics of the organ. For example, a patient's liver can be tested by injecting a solution containing urea.

Perivascular measurements may also be made on either an artery or a vein, or both, but these measurements are made externally of the vessel, as noted above. Sensors for this purpose may be ultrasonic flow meters such as those manufactured by Transonic Systems, Inc., Ithaca, N.Y. or other suitable flow meters utilizing ultrasonic waves for measurement of flow. In perivascular systems, however, the material and geometric characteristics of the vessel itself affect the measurements, so compensation is required, as will be described hereinbelow.

In another form of the invention, referred to herein as a clamp-on measurement system, measurements of blood are made outside the patient's body; for example, in tubing leading from the patient's vascular system to a blood treatment system such as a dialysis machine. In such a system, blood is drawn from the patient, passed through suitable tubing to a dialysis filter and is then returned through tubing to the patient, usually to the same vessel from which the blood being treated was initially drawn, but downstream of the withdrawal site. Clamp-on sensors such as Transonic Systems' ultrasonic flow meters are suitable for measuring blood flow through the tubing, but the measured parameters are functions not only of blood characteristics, but of tube material and geometry. In such a case, calibration of the system is required to eliminate the effects of the tubing. As with intravascular and perivascular systems, arterial or venous measurements, or both, may be made in the clamp-on system, with injections of indicator material in either the artery or the vein, or both, to permit determination of various blood characteristics as well as permitting measurement of the effectiveness of a treatment system.

Ultrasonic sensors measure sound velocity dilution as the indicator material is carried past the sensor by the bloodstream, and changes in sound velocity are plotted to permit calculation of various blood parameters. The time at which the indicator material reaches the sensor after injection, the area under the plotted curve representing the changes in sound velocity at the sensor, and the amplitude of the measurement all provide information concerning the blood characteristics, in accordance with the invention.

BRIEF DESCRIPTION OF THE DRAWINGS

The foregoing, and additional objects, features, and advantages of the present invention will become apparent to those of skill in the art from the following detailed description of preferred embodiments thereof, taken in conjunction with the accompanying drawings, in which:

FIGS. 7–9 are diagrammatic illustrations of sensors suitable for use with the catheter of FIG. 1;

FIGS. 28 and 29 are graphical illustrations of sound velocity and blood impedance changes for use in calibrating the measurement of lung water;

FIGS. 30 and 31 are graphical illustrations of arterial sound velocity and blood impedance changes responsive to a calibrating intravenous injection of hypertonic saline solution for determination of lung water;

DESCRIPTION OF PREFERRED EMBODIMENT

Figure 1:
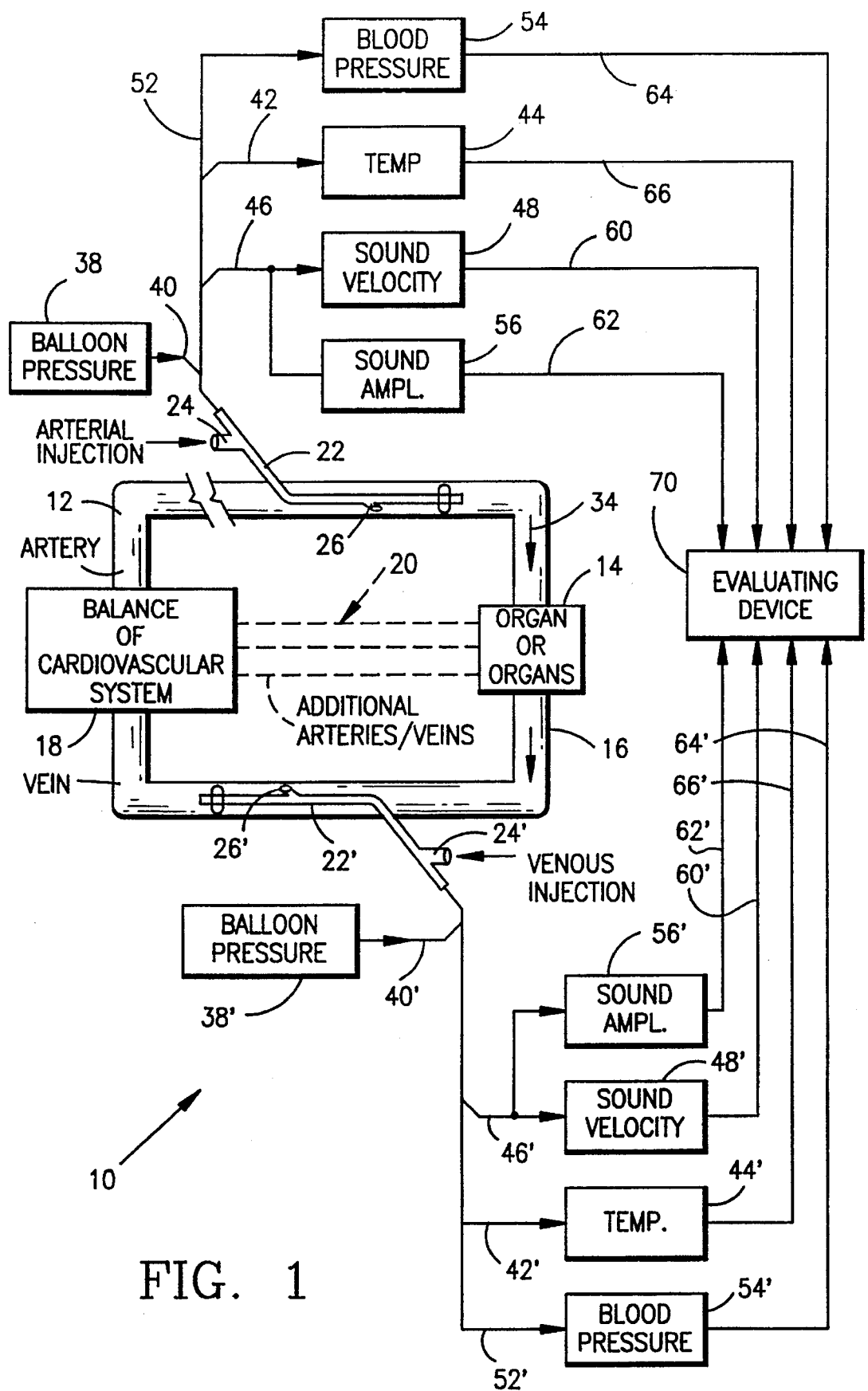
FIG. 1 is a diagrammatic illustration of an intravascular blood measurement system utilizing sound velocity measurements.

Turning now to a more detailed description of the present invention, there is illustrated in FIG. 1 in diagrammatic form an intravascular blood measurement system 10 utilizing sound velocity measurements for determining blood characteristics. The ultrasound velocity in blood, $C_b$, can be described as a function of total protein concentration P, and concentration of ions I, (D. Schneditz and T. Kenner, J.Acoust.Soc.Am. 86 (6), pp. 2073–2081, (1989) "A Sound-Speed Sensor for the Measurement of Total Protein Concentration in Disposable, Blood-Perfused Tubes") and by V. A. Del Grosso and C. W. Mader, J. Acoust. Soc. Am. 52, 961–974 (1972) "Speed of Sound in Sea Water Samples"), and may be expressed as follows:

$$C_b = A_0 + A_1 P + A_2 P^2 + A_3 I \quad \text{(Eq. 1)}$$

$$P = N/V_b \quad \text{(Eq. 2)}$$

where $A_0$, $A_1$, $A_2$, and $A_3$ are known coefficients that are functions of temperature; N is the amount of protein in blood volume $V_b$; and I is the average concentration of ions in plasma and erythrocytes.

Figure 2:
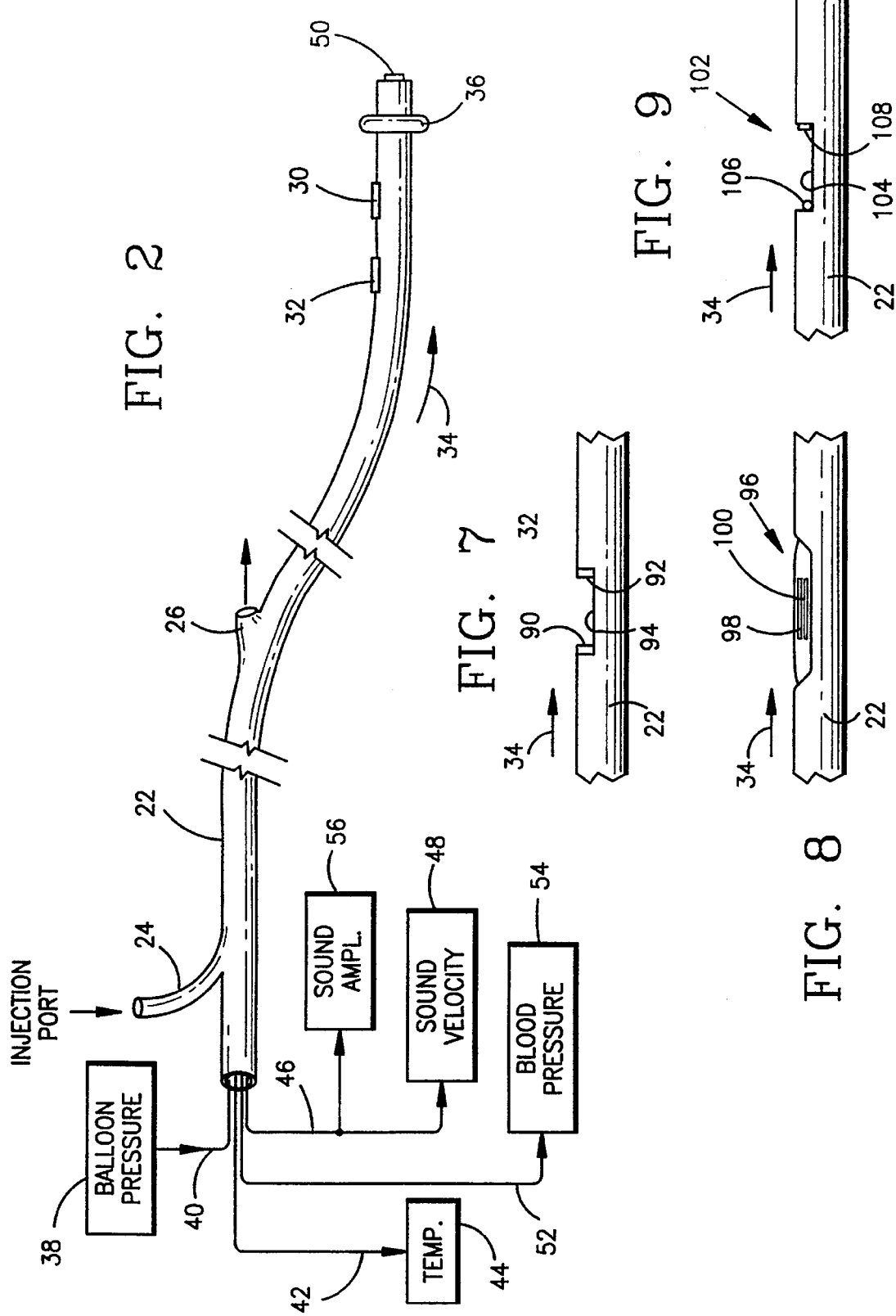
FIG. 2 is a diagrammatic illustration of a catheter for use in the system of FIG. 1.

The cardiovascular system of a patient is indicated in FIG. 1 by a vessel 12 which may be an artery leading to a patient's organs or to a selected organ indicated by block 14. A vessel 16 is a vein carrying blood away from the organ 14 to other parts of the cardiovascular system indicated by block 18. Additional arteries or veins indicated in phantom at 20 may also lead to the organ 14. An arterial catheter 22 is inserted into the artery 12, in accordance with one embodiment of the present invention, to provide a passageway for injecting an indicator material such as a saline solution into the artery at a selected location. The catheter thus includes an inlet port 24 accessible outside the patient's body and an outlet port 26 located on the catheter for positioning within a vessel for this purpose. The catheter also includes a plurality of sensors, illustrated in greater detail in FIG. 2, to which reference is now made.

As illustrated, the catheter preferably incorporates a conventional temperature sensor 30 for measuring blood temperature, and a sound velocity sensor 32 for determining the velocity of ultrasonic waves in the blood flowing past the catheter. These two sensors are located downstream of the catheter outlet 26 so that indicator material injected into the bloodstream will pass by the sensors. The direction of blood flow in the artery 12 and past the catheter 22 is indicated by arrows 34 in FIGS. 1 and 2. It is noted that a balloon 36 may be provided on the catheter for securing it at a desired location, the expansion of the balloon being controlled by a source 38 of fluid under controlled pressure connected to the balloon internally of the catheter as by way of line 40. The temperature sensor 30 is connected by way of lead 42 to a suitable temperature detecting circuit 44 while the sound velocity sensor 32 is connected by way of lead 46 to a suitable sound velocity detecting circuit 48. In addition to these sensors, a blood pressure sensor 50 may also be provided on the catheter 22 and connected by way of lead 52 to a blood pressure detector 54. If desired, an additional measurement of sound amplitude may be made by means of sound amplitude detector 56 also connected by way of lead 46 to sensor 32.

As illustrated in FIG. 1, each of the detectors 44, 48, 54, and 56 is connected by a corresponding one of leads 60, 62, 64, and 66 to an evaluating device 70, which may be a personal computer for carrying out the curve plotting and calculations described herein.

The catheter with its sound velocity sensor 32, when placed in the blood vessel 12, provides a direct measure of the velocity of ultrasound in the blood carried by the artery, and permits a determination of blood parameters such as the total protein concentration in the blood and its changes based on sound velocity changes resulting from the injection of an indicator material and the resultant dilution of the blood. The dilution of flowing blood by the injection of an isotonic saline solution, for example, injected at body temperature, decreases the blood sound velocity in accordance with the following equation:

$$\Delta C_b(t) = A_1 * \Delta P(t) + 2A_2 P * \Delta P(t) \quad \text{(Eq. 3)}$$

where P is the total protein concentration in the blood before the injection. The change in protein concentration with time $\Delta P(t)$ can be calculated from equation 2 and gives the following result:

$$\Delta P(t) = \frac{N}{V_b + V_{isot.}(t)} - \frac{N}{V_b} = -\frac{P * V_{isot.}(t)}{V_b} \quad \text{(Eq. 4)}$$

where $V_b$ is the volume of blood that mixes with the indicator and $V_{isot.}(t)$ is the amount of indicator at time (t) in the blood. The resulting change in blood sound velocity can then be rewritten as follows:

$$\Delta C_b(t) = -\frac{V_{isot.}(t)}{V_b}(A_1 P + 2A_2 P^2) \quad \text{(Eq. 5)}$$

Figure 3:
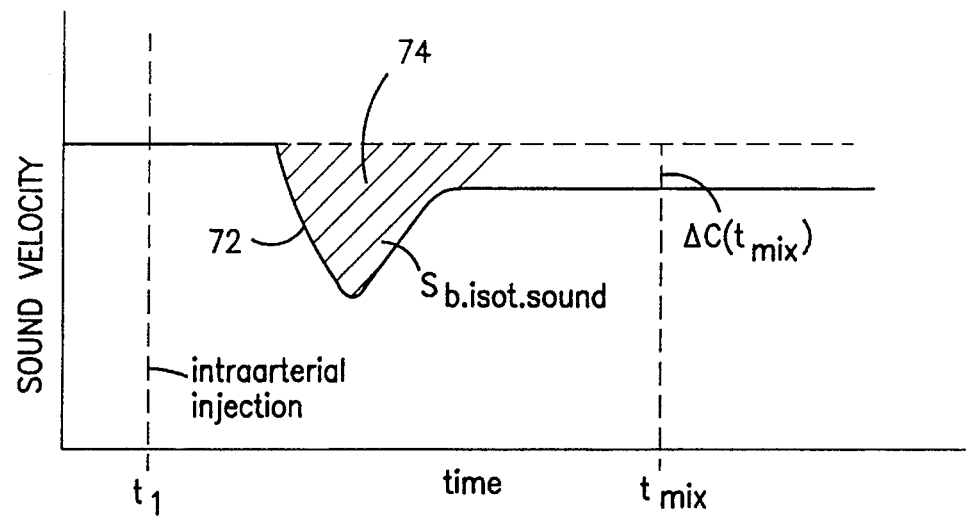
FIG. 3 is a dilution curve showing the change in blood sound velocity following injection of an indicator material.

Summation over a period of time such as one minute will give the average flow through the system during this time, as follows:

$$Q = \frac{V_{isot.}(A_1 P + 2A_2 P^2)}{S_{b.isot.sound.}} \quad \text{(Eq. 6)}$$

where $S_{b.isot.sound.}$ is the area under a dilution curve representing through the system during the given period of time, and $V_{isot.}$ is the changes in blood sound velocity over time, Q is the average flow volume of the injected indicator solution. FIG. 3 illustrates such a dilution curve 72, showing changes in sound velocity due to an injection of an indicator medium at time $t_1$ from injection outlet 26 of catheter 22. The change in blood sound velocity is measured at sensor 32 (FIG. 2) downstream of the injection site. The cross-hatched area 74 under the curve 72 is determined in evaluating device 70 to permit calculation of the average flow through the system in accordance with Eq. 6.

For the sound velocity sensor located in an artery within the blood circulating system of a patient; for example, in a pulmonary artery, and for an intravenous injection $V_{isot.}$ at time $t_1$, the measured value Q from equation 6 is the cardiac output CO, so that Q=CO. For the intraarterial injection, this measured flow is also the blood flow through the patient's organ or organs. The thermal sensor 30 on the catheter increases the accuracy of temperature. By directly measuring blood temperature, therefore, measurement because the velocity of sound in blood varies with more accurate calculations of the "A" coefficients in equation 1 for protein and for CO calculations in equation 6 are obtained.

Figure 4:
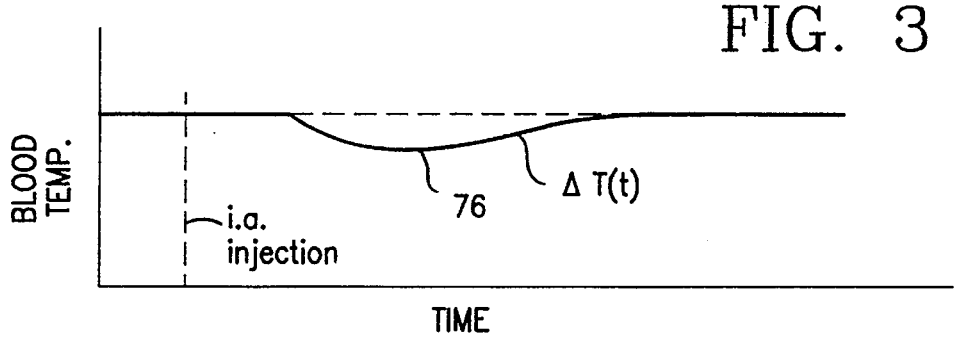
FIG. 4 is a temperature dilution curve for the system of FIG. 1.
Figure 5:
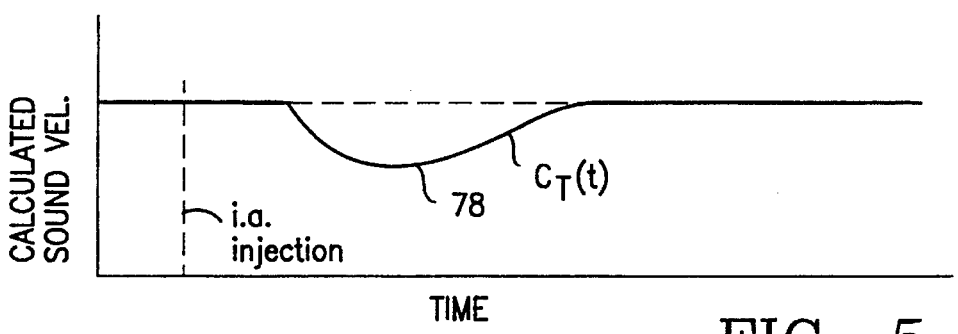
FIG. 5 is a curve representing calculated sound velocity changes due to temperature.
Figure 6:
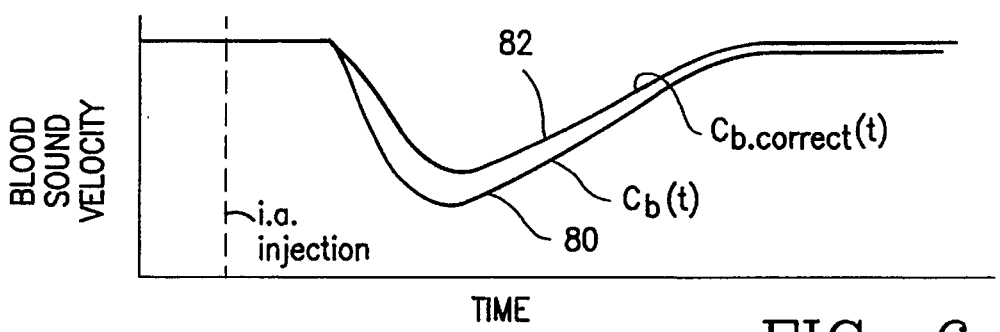
FIG. 6 is a sound velocity dilution curve corrected for temperature variations.

If the temperature of the injected indicator medium is not equal to body temperature; for example is colder, then measurements to provide the curves of FIGS. 4, 5, and 6 may be made to correct the recorded sound velocity to obtain highly accurate blood parameter calculations. Thus, variations in blood temperature at sensor 30 following the intravenous injection at port 26 are measured and plotted, as illustrated by curve 76 in FIG. 4, to provide a temperature dilution curve ΔT(t). This dilution curve 76 is used to calculate sound velocity changes due to the influence of temperature changes, the calculations being indicated by curve 78 in FIG. 5. This curve provides a calculated temperature correction $C_T(t)=A\Delta T(t)$, where A is known, which is used to correct a recorded sound velocity dilution curve 80 (FIG. 6), indicated by $C_b(t)$, to obtain a highly accurate cardiac output value indicated by curve 82 and providing the value $C_{b.correct}(t)$.

Because an isotonic solution leaves an intravascular space slowly, as indicated by curve 72 in FIG. 3, this curve can also be used to calculate blood circulating volume (BCV), which can be calculated from FIG. 3 as follows:

$$BCV=CO*S_{b.isot.sound}/\Delta C(t_{mix}) \quad \text{(Eq. 7)}$$

where $\Delta C(t_{mix})$ is the decrease of sound velocity produced when there is a full mixing of the indicator material with the blood in the artery 12.

As further illustrated in FIG. 1, a second catheter 22' may also be incorporated in the blood measurement system 10, this catheter being inserted in vein 16 for use in measuring blood flow therein. The catheter 22' is substantially identical to catheter 22 with similar elements being similarly numbered, but primed. The measurements available with the use of catheter 22' will be described hereinbelow.

Sensors usable with the catheter 22 are illustrated diagrammatically in FIGS. 7, 8, and 9. FIG. 7 illustrates a sound velocity sensor 32 having an ultrasonic sound wave generating crystal 90 and a similar receiving crystal 92 located on opposite ends of a cavity 94 formed in the surface of the catheter. Sound waves emitted by crystal 90 are received by crystal 92, the sound waves traveling through the blood surrounding the catheter and filling the cavity 94. The blood flow carries the indicator medium, as described above, which changes the velocity of the sound waves crossing from one end to the other of cavity 94. The output from sensor 32 is supplied to the sound velocity detector 48 which measures the time required for the waves to travel from transmitter 90 to receiver 92, thereby providing the data for plotting the curve of FIG. 3.

FIG. 8 similarly illustrates an electrical impedance sensor 96 located on the surface of catheter 22, the sensor incorporating a plurality of electrically conductive strips 98, 100 which measure the conductivity of the blood 34 passing the sensor. This conductivity measurement allows detection of the impedance of the blood by a corresponding detector (not shown). FIG. 9 illustrates an optical sensor 102 located in a cavity 104 on a surface of catheter 22. The sensor includes a light source 106 at one end of the cavity and a light sensor 108 at the other end of the cavity for detecting the optical density of the blood 34 passing the catheter 22. A suitable detector connected to sensor 108 may be provided to produce measurements of the optical characteristics of the blood. These and other known sensors may be used with catheter 22 to provide the required blood characteristics.

Figure 10:
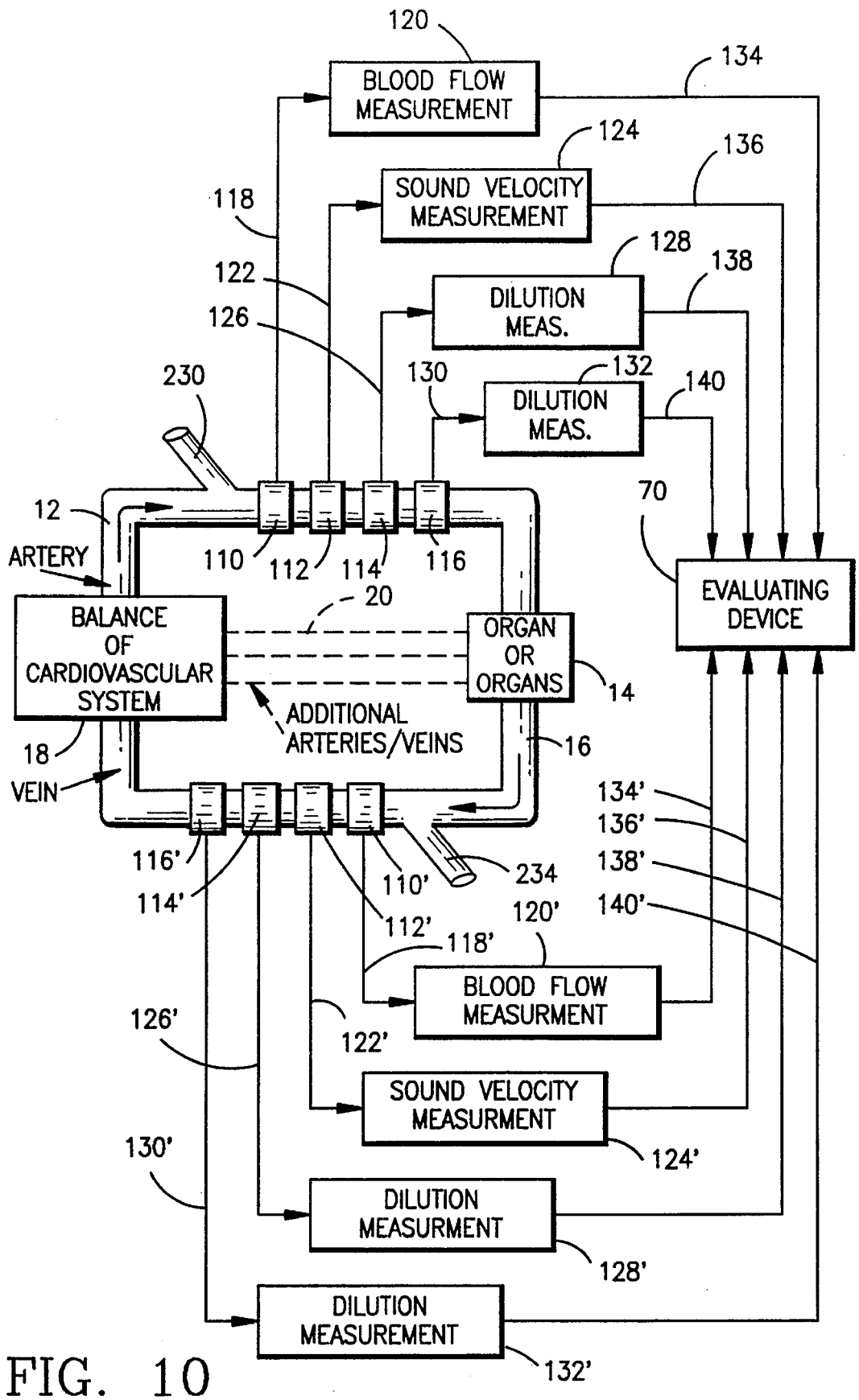
FIG. 10 is a diagrammatic illustration of a perivascular blood measurement system utilizing sound velocity measurements.

A modification of the system of FIG. 1 is illustrated in FIG. 10, wherein the system utilizes perivascular measurements instead of the intravascular measurements obtained by the catheter of FIG. 1. Elements of FIG. 10 common to FIG. 1 carry similar identifying numerals. In the perivascular system of FIG. 10, clamp-on sensors 110, 112, 114, and 116 are provided on artery 12, with corresponding sensors 110', 112', 114', and 116' being provided on the exterior of vein 16. Sensors 110 and 110' are blood flow measurement sensors which provide output signals by way of lines 118 and 118' to corresponding blood flow measurement detectors 120 and 120'. Each of the blood flow sensors may be a Bypass Flow Meter model HT 109 or model T106 produced by Transonic Systems, Inc., Ithaca, N.Y., for example. Sensors 112 and 112' measure sound velocity in the bloodstream of the artery 12 and the vein 16, respectively, and produce outputs on their corresponding lines 122 and 122' to corresponding sound velocity measurement detectors 124 and 124'. The sensors 112 and 112' each may be a sensor such as model No. DT 106, also available from Transonic Systems, Inc.

Sensors 114 and 114' are blood dilution sensors which are connected by way of lines 126 and 126' to dilution measurement detectors 128 and 128. Similarly, sensors 116 and 116' are additional blood dilution sensors and produce output signals on lines 130 and 130' to corresponding dilution detectors 132 and 132'. The outputs of detectors 120, 124, 128, and 132 are connected by way of lines 134, 136, 138, and 140, respectively, to the evaluating device 70, and in similar manner detectors 120', 124', 128', and 132' are also connected to the evaluating device. The dilution sensors 114, 114' and 116, 116' may be any of a variety of sensors for detecting various blood characteristics. For example, sensors 114 and 114' may be electrical impedance sensors, and sensors 116, 116' may be optical sensors, the particular sensors selected being dependent on the blood characteristics of interest.

Figure 11:
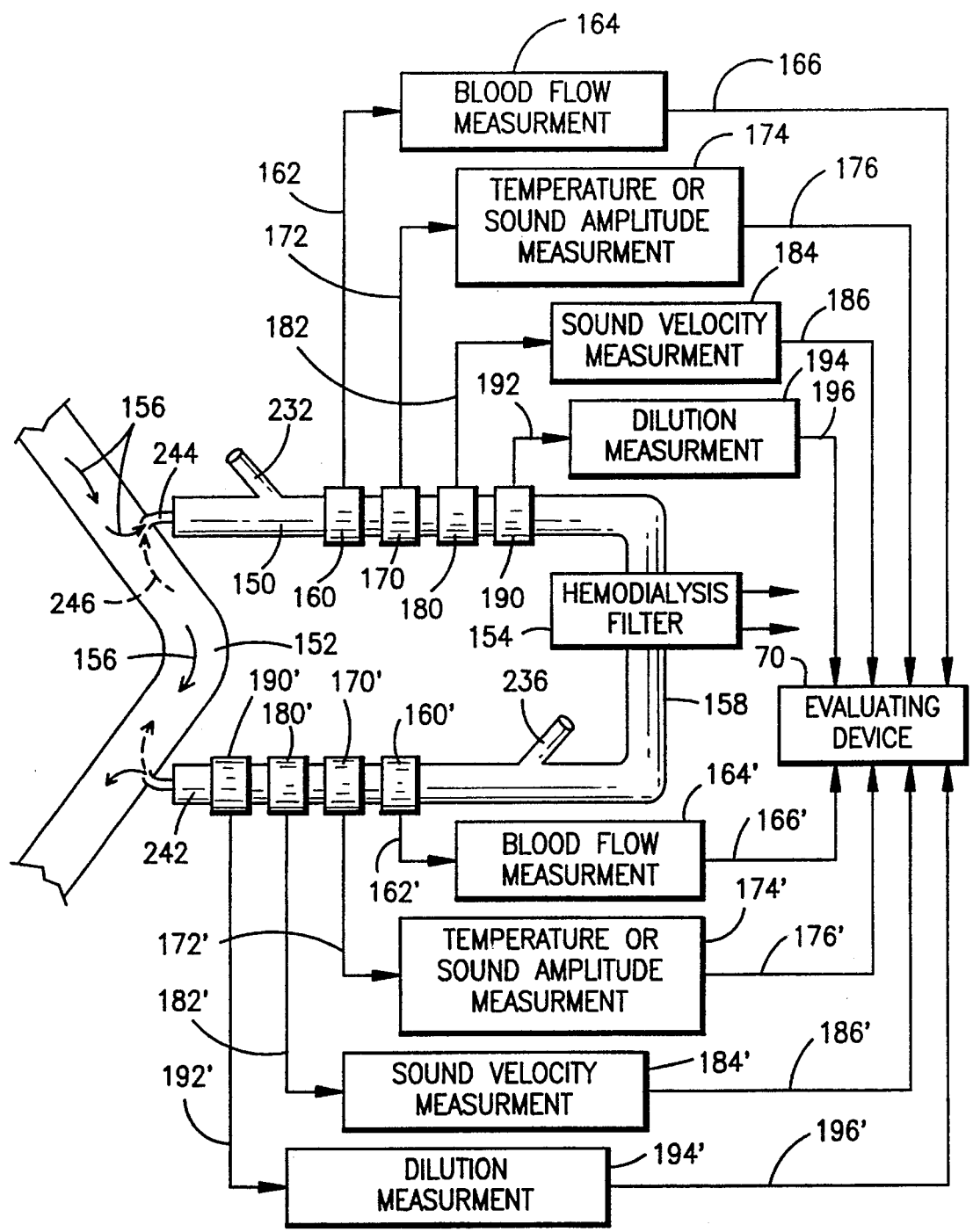
FIG. 11 is a diagrammatic illustration of a clamp-on sensor system utilizing sound velocity measurements.

A still further modification of the invention is illustrated in FIG. 11, wherein the exterior, or clamp-on sensors utilized in the system of FIG. 10 are used to measure blood flow through a conduit, or tubing, 150 leading from a vessel 152 of a patient to external, i.e., extracoporeal, equipment such as a hemodialysis filter 154. The vessel 152 may be an artery of a patient or a shunt placed in the cardiovascular system of a patient. As indicated by arrows 156, a portion of the blood flowing through the vessel 152 is drawn through inlet, or arterial tubing 150 for delivery to the hemodialysis filter 154. The blood which passes through the filter is then returned to vessel 152 by way of outlet tubing 158 which may be referred to as the venous tubing. Surrounding, or clamped onto, the arterial tubing 150 are a plurality of blood sensors such as a blood flow sensor 160 connected by way of line 162 a blood flow detector 164. Sensor 160 is similar to the blood flow sensor 110 of FIG. 10 and provides an output on line 162 which is a measure of the volume of blood flow flowing through tubing 150. The signal from detector 164 is supplied by way of line 166 to the evaluating device 70 which carries out the determinations of blood parameters in accordance with the relationships described herein.

Also clamped around arterial tubing 150 is a temperature sensor 170 which provides an output by way of line 172 to a detector 174, the output of which is supplied by way of line 176 to the evaluating device 70. The temperature sensor measures the temperature of the blood flowing through tubing 150. Alternatively, the sensor 170 may be a sound amplitude sensor and detector 174 may provide a measure of variations of sound amplitude changes.

A third sensor 180 is clamped around tube 150 for dilution measurement. Although this sensor may be any one of the dilution sensors discussed above, a sound velocity sensor for changes in sound velocity in the bloodstream is preferred. The output from sensor 180 is supplied by way of line 182 to a sound velocity detector 184, the output of which is supplied by way of line 186 to the evaluating device 70.

A fourth sensor 190 is also provided on arterial tubing 150. This sensor is another dilution sensor, and may be an optical sensor, an impedance sensor, or the like for measuring additional blood parameters, with the output from the sensor being supplied by way of line 192 to a corresponding detector 194, the output of which is supplied by way of line 196 to the evaluating device 70.

The venous tubing 158 may also carry similar sensors indicated at 160', 170', 180', and 190', the outputs of which are supplied to corresponding detectors 164', 174', 184' and 194', with the detected signals being supplied to the evaluating device 70.

Figure 12:
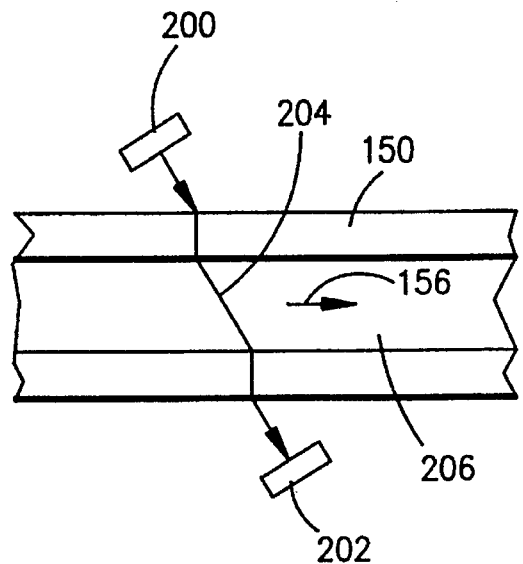
FIGS. 12–15 are diagrammatic illustrations of various blood measurement sensors which may be utilized in the systems of FIGS. 10 and 11.

FIGS. 12–15 illustrate various clamp-on sensors which may be utilized in the systems of FIGS. 10 and 11. Thus, FIG. 12 illustrates an ultrasonic sensor, which may be used as sensor 180 or 190, for example, having an ultrasonic wave generating crystal 200 positioned on one side of tubing 150 and a corresponding receiving crystal 202 located on the opposite side of the tubing. Sound waves 204 generated by crystal 200 travel through the wall of tubing 150, through the blood 156 flowing within the central passageway 206 of the tubing, back through the wall of the tubing and are received by crystal 202. As is known, the received ultrasound varies with changes in the acoustical characteristics of the blood flow.

Figure 13:
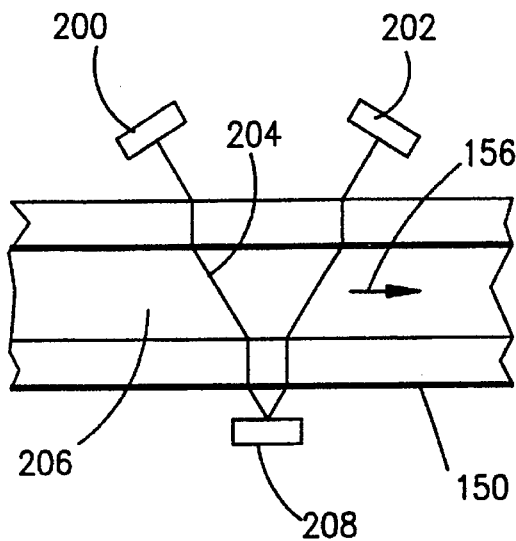

FIG. 13 illustrates a second type of ultrasonic sensor, also suitable for use as the sensor 180 or 190 in FIG. 11, for example, but differing in that the transmitting crystal 200 and the receiving crystal 202 are located on the same side of the tube 150. In this device, the wave 204 emitted by crystal 200 is transmitted through the tubing and the bloodstream 156, and is reflected by a mirror 208 back through the tubing and the bloodstream to the receiving crystal 202.

Figure 14:
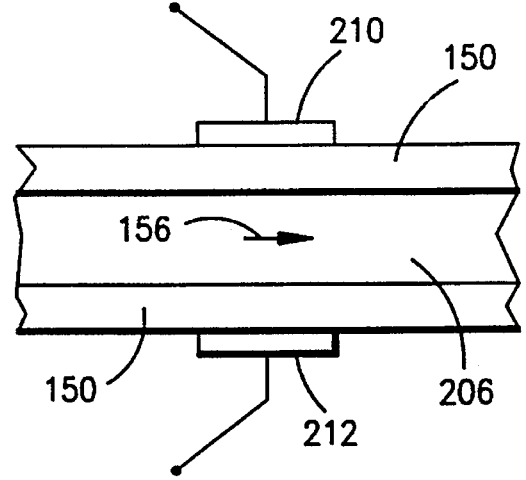
Figure 15:
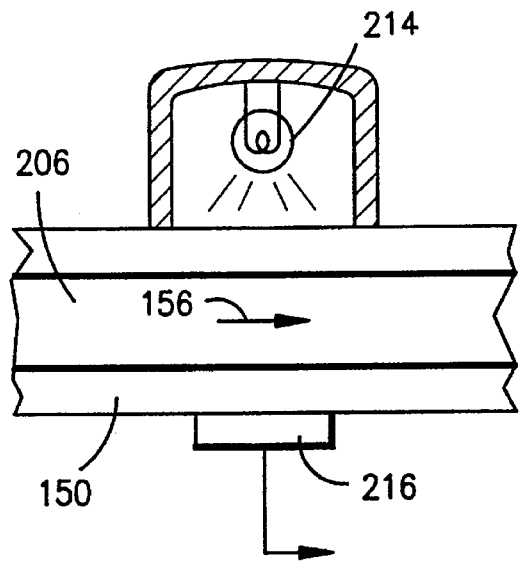

FIG. 14 illustrates an electrical impedance sensor which also may be used as the sensor 180 or 190 in FIG. 11. This sensor includes a pair of electrodes 210 and 212 located, for example, on opposite sides of tubing 150 for measuring the electrical conductivity of the bloodstream 156. Still another sensor suitable for use in the system of FIG. 11 is a clamp-on optical sensor such as that illustrated in FIG. 15, which may include a light source 214 on one side of the tubing 150 and a light sensor 216 on the opposite side for measuring the optical density of the bloodstream.

In the embodiments of both FIG. 10 and FIG. 11, the ultrasonic waves of the sound sensors, such as sensors 110 and 112 in FIG. 10, and sensors 160 and 180 in FIG. 11, pass through the conduit, which is either the vessels 12, 16, or the tubing 150, 158 as well as the blood. In such cases, the measured sound velocity is a function of the geometry of the tube/vessel and its acoustical properties, as well as the acoustical properties of the blood. The relationship between the measured sound velocity C and an unknown blood sound velocity $C_b$, can be stated as:

$$C=(C_t*l_t+C_b*l_b)/(l_t+l_b) \quad \text{(Eq. 8)}$$

where $C_t$ is the average velocity of ultrasound through the material of the tube/vessel, where $i_t$ is the equivalent path length of ultrasound through the tube/vessel, and where $I_b$ is the equivalent path length through the blood.

In order to take into account the effects of the tube/vessel acoustical properties, it is necessary to calibrate the systems of FIGS. 10 and 11. For the system of FIG. 11, the tube system can be calibrated by filling it with a solution of known sound properties, such as a saline solution, and measuring the sound velocity. This measurement can then be compared with the velocity of sound in the blood, and the relationship between C and $C_b$, can be found. This relationship will be valid for a constant temperature.

If, during dialysis for example, the blood temperature changes, it will change the sound velocity not only in the blood, but in the tube, as well. This will decrease the accuracy of the measurements because of the strong influence of tube temperature on sound velocity, the velocity changing in the range of 3 to 7 m/s/°C. for different materials. Because of this, the real change in sound velocity due, for example, to a variation in protein concentration $\Delta C(t)$ will be the difference between the measured changes in ultrasound velocity $\Delta C_m(t)$ and the change due to the influence of temperature $\Delta C_m(t)$, which may be expressed as follows:

$$\Delta C(t)=\Delta C_m(t)-\Delta C_T(t) \quad \text{(Eq. 9)}$$

Figure 16:
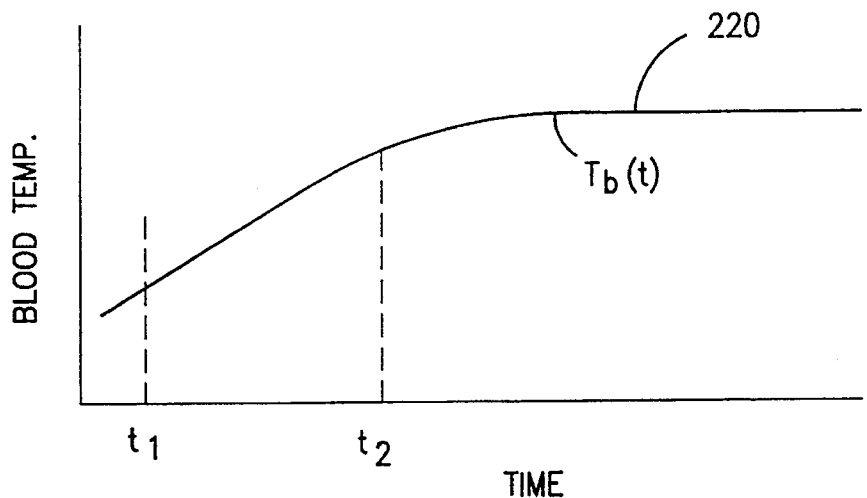
FIG. 16 is a graphical illustration of a change in blood temperature over time in a tube.
Figure 17:
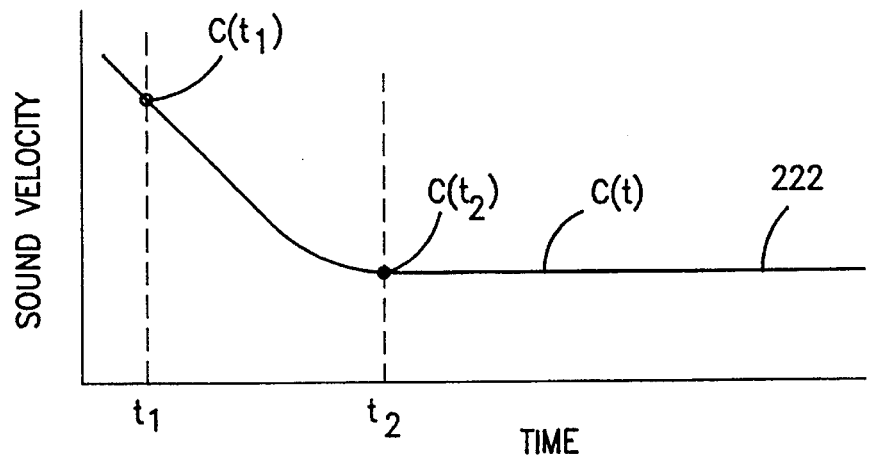
FIG. 17 is a graphical illustration of a change in tube sound velocity due to the temperature change of FIG. 16.
Figure 18:
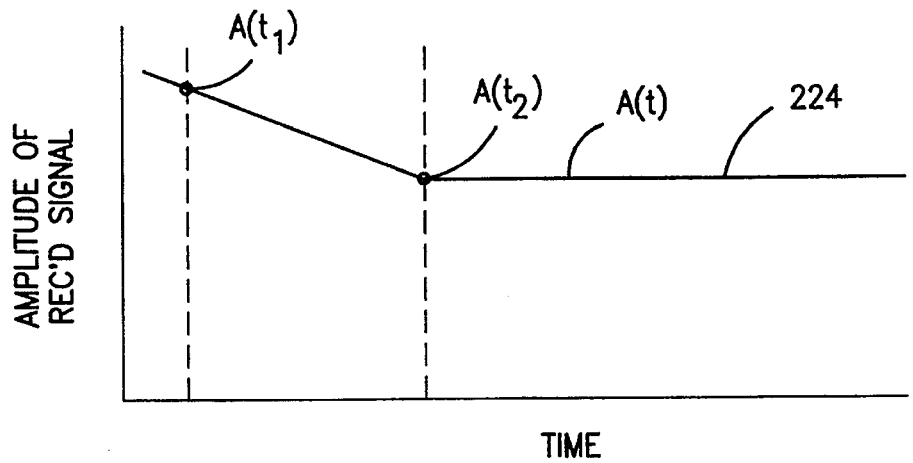
FIG. 18 is a graphical illustration of a change in amplitude of received sound waves due to the tube temperature change of FIG. 16.

Temperature changes in the bloodstream, such as the changes illustrated in FIG. 16 by curve 220, may occur during treatment. As noted above, a temperature change will also influence both the ultrasound velocity in the tube itself, and the attenuation of sound in the tube itself, as illustrated by curve 222 in FIG. 17 and curve 224 in FIG. 18. Thus, for example, an increase in blood temperature $T_b$ (curve 220 in FIG. 16) heats the tube, making it softer and changing the conditions for sound wave propagation through the tube material. As illustrated by curve 222 in FIG. 17 the ultrasound velocity drops with increased temperature and, as illustrated by curve 224 in FIG. 18, attenuation of the signal increases, causing the amplitude A of the received signal to drop. Experiments have shown that because these changes arise from the same cause, they behave synchronously and may be expressed as $C_T(t)$, the change in sound velocity with temperature. The recorded changes in amplitude of the received acoustical signals are only due to tube temperature changes, because blood does not attenuate sound waves up to about 10 to 15 MHz; accordingly, up to these frequencies, changes in blood parameters such as protein content don't influence sound attenuation. This makes it possible to compensate for the influence of temperature on the measured ultrasound velocity by recording the changes in the amplitude of the received sound signal $\Delta A(t)$ due to changes in temperature in accordance with the following equation:

$$\Delta C_T(t)=K_T*\Delta A(t) \quad \text{(Eq. 10)}$$

where $K_T$ is a coefficient which can be calculated for the type of tubing that is used in the blood treatment system. Such calculations may be made prior to use of the tubing or may be calculated during use in, for example, dialysis as a ratio of the slope of the sound velocity and the slope of the sound amplitude at the beginning of the dialysis procedure when the tube is being heated or cooled by the blood, as expressed in the following equation:

$$K_7 = [C(t_1) - C(t_2)] / [A(t_1) - A(t_2)] \quad \text{(Eq. 11)}$$

It is noted that the perivascular system of FIG. 10 cannot be precalibrated because the vessel wall size and its properties are unknown. Accordingly, the perivascular probe must be calibrated during dialysis or other treatment.

Another way to calibrate the perivascular sensors or the clamp-on tube sensors of FIGS. 10 and 11 is to make a calibration injection of a known indicator material directly prior to the location of the sound velocity sensor while simultaneously measuring the blood flow through the tube/vessel. A calibration injection into the arterial line, for example by way of arterial inlet ports 230 or 232 in the systems of FIGS. 10 and 11, respectively, will change the measured sound velocity in the arterial sensors 112 or 180 as follows:

$$\Delta C(t) = \Delta C_b(t) * l_b / (l_t + l_b) \quad \text{(Eq. 12)}$$

or $$S_{A.cal.isot.sound} = S_{A.b.cal.isot.sound} * l_b / (l_t + l_b) \quad \text{(Eq. 13)}$$

where $S_{A.cal.isot.sound}$ is the measured sound velocity dilution area generated by blood sound velocity dilution changes ($S_{A.b.cal.isot.sound}$). From equations 6 and 13 the average flow through the tube/vessel during the time when the indicator passes is expressed as follows:

$$Q_{A.cal.} = \frac{(A_1 P + 2A_2 P_2) V_{A.cal.isot.} * l_b}{S_{A.cal.isot.sound.} (l_t + l_b)} \quad \text{(Eq. 14)}$$

where $Q_{A.cal.}$ is the average flow through the tube/vessel and $V_{A.cal.isot.}$ is the volume of the calibrating injection.

Figure 19:
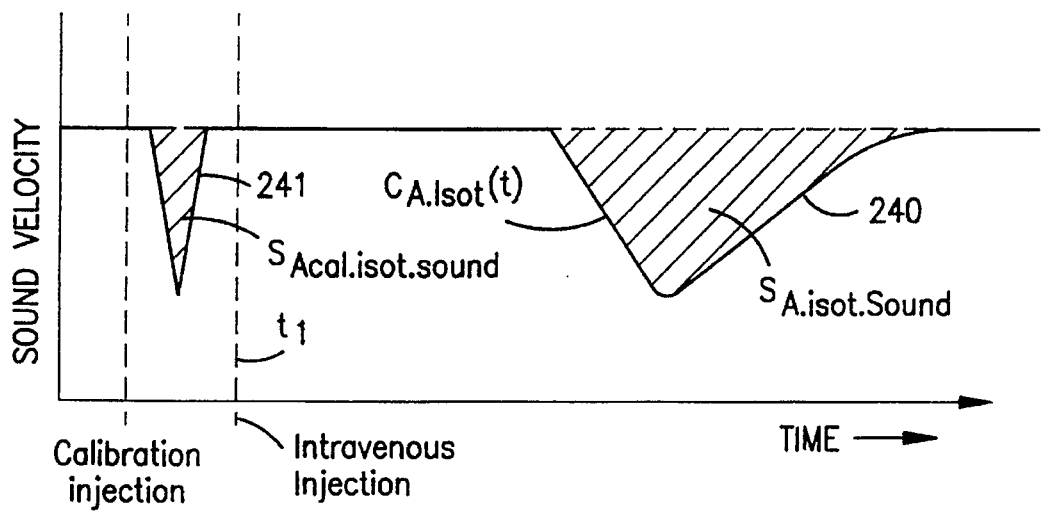
FIG. 19 is a graphical illustration of sound velocity changes produced by injections of indicator material.

The sensors carried by the vein 16 or the venous tube 158 in FIGS. 10 and 11, respectively, may also be used to calculate various blood flow parameters. Thus, for example, by analogy with equation 6, the cardiac output CO can be calculated after an injection at body temperature of an isotonic saline indicator solution into the venous port (by way of catheter 234 in FIG. 10 or 236 in FIG. 11) and detecting the indicator at sensors 112' or 180'. Thus, from equations 6, 13, and 14, the cardiac output is calculated as follows:

$$CO = \frac{V_{V.isot.} S_{A.cal.isot.sound.} * Q_{A.cal.}}{V_{A.cal.isot.} S_{A.isot.sound.}} \quad \text{(Eq. 15)}$$

where $S_{A.isot.sound.}$ is the measured sound velocity dilution area under a curve 240 generated by the measurement of dilution produced by an intravenous injection of a volume $V_{V.isot.}$ at $t_1$ illustrated in FIG. 19.

Prior to the foregoing measurement, a measured sound velocity dilution area $S_{A.cal.isot.sound.}$ is produced by curve 241 in FIG. 19 and, as illustrated, follows closely after a calibration injection upstream of the sensor.

The cardiac output can be calculated from a single intravenous injection at port 236, when the dilution sensors are located on both the arterial and venous parts of the system and are closely matched, as illustrated in FIG. 11.

Figure 20:
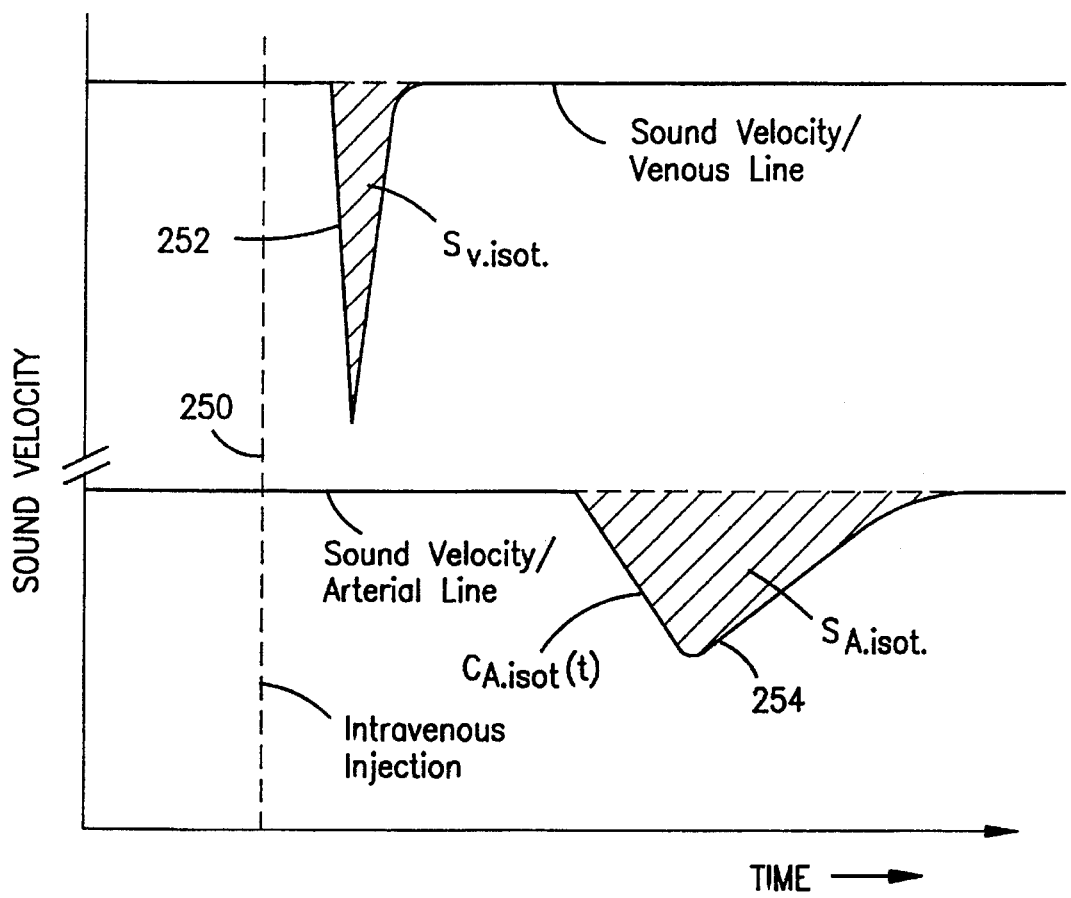
FIG. 20 is a graphical illustration of changes in venous and arterial sound velocities following an intravenous injection of an isotonic solution in the system of FIG. 11 for determining cardiac output.

The cardiac output can be calculated from a single intravenous injection ($Q_{A.cal.isot.} \rightarrow Q_{V.isot.}$ and $S_{A.cal.isot.} \rightarrow S_{V.isot.}$) by obtaining the measurements illustrated in FIG. 20. As there illustrated, an intravenous injection is made at a time $t_1$ indicated by vertical line 250, and shortly thereafter sound velocity sensor 180' detects in the venous line the dilution illustrated by curve 252. A portion of the indicator material is then recirculated to the arterial line 150 where it is detected by sensor 180, as indicated at curve 254. The cardiac output CO can then be calculated as follows:

$$CO = \frac{Q_{V.isot.} * S_{V.isot.}}{S_{A.isot.}} \quad \text{(Eq. 16)}$$

where $Q_{V.isot.}$ is the blood flow in the venous line during the isotonic injection and $S_{V.isot.}$ is the dilution area generated in the venous sensor. These calculations of cardiac output are independent of the properties of the tubing/vessel and the blood.

By analogy with equation 5, relatively small changes of circulating blood volume can be measured in the systems illustrated in FIGS. 1, 10, and 11. In the system of FIG. 1, blood volume can be measured by intravascular sound sensors on catheter 22 as follows:

$$\Delta C(t) = -\frac{\Delta V_b(t)}{V_b} (A_1 P + 2A_2 P^2) \quad \text{(Eq. 17)}$$

where $\Delta V_b$ is the change in blood volume. In similar manner, the change of blood volume can be calculated for the configurations of FIGS. 10 and 11 from equations 12, 14, and 17, as follows:

$$\frac{\Delta V_b(t)}{V_b} = \frac{\Delta C(t) * V_{A.cal.isot.}}{S_{A.cal.isot.} * Q_{A.cal.}} \quad \text{(Eq. 18)}$$

The foregoing illustrates that the monitoring of changes in ultrasound velocity $\Delta C(t)$ due to indicator dilution permits the monitoring of total protein changes (equation 3) and relative changes of blood volume not only with intravascular catheters (equation 17), but noninvasively, as during a dialysis procedure (equation 18). In each case, this is done with a single calibration injection and a single measurement injection. This is important in dialysis procedures to prevent the unpleasant effects of fluid unbalancing in such a procedure.

Figure 21:
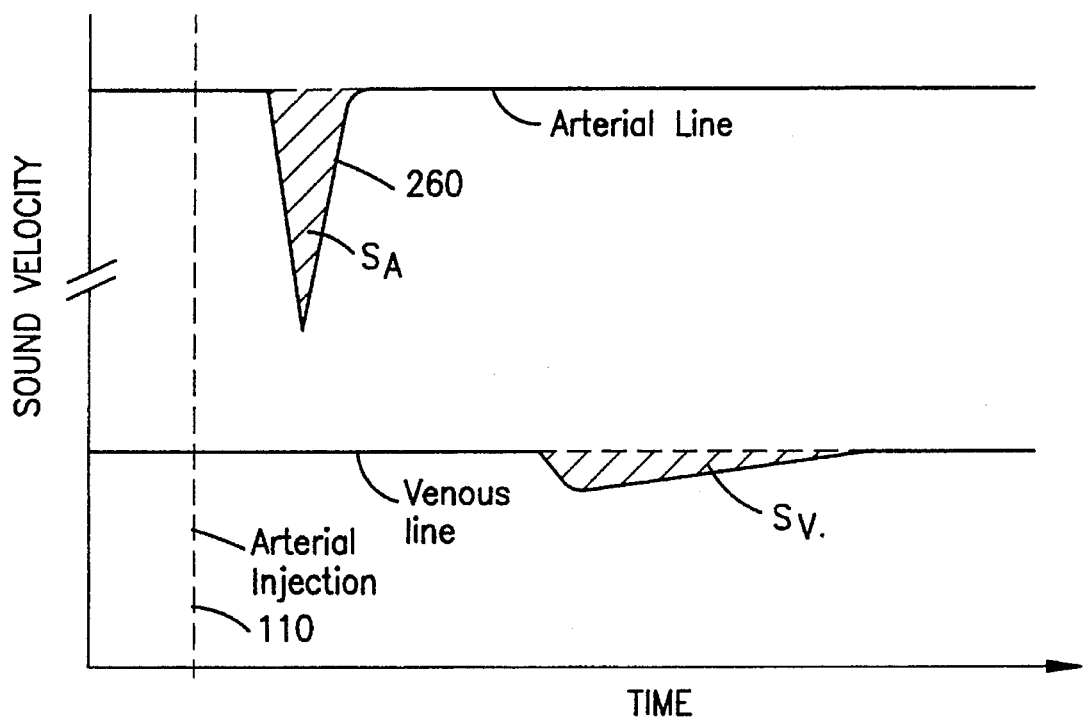
FIG. 21 is a graphical illustration of changes in venous and arterial sound velocities following an arterial injection of a solution for determining organ or filter clearance.

The systems of FIGS. 1, 10, and 11 may also be used to determine the clearance $K_{clear}$ of different solutes passing through a patient's organ or organs 14 or through blood treatment equipment such as the hemodialysis filter 154. For this purpose, a suitable solution is injected into the appropriate arterial input port 24, 230, or 232, and the dilution signals and flows are recorded in both the arterial and venous lines, as indicated by curves 260 and 262 in FIG. 21. The changes that take place in the solution as it passes through the hemofilter/organ is obtained by the following equation:

$$K_{clear} = 1 - Q_V * S_V / (Q_A * S_A) \quad \text{(Eq. 19)}$$

where $Q_A$ and $Q_V$ are the corresponding blood flows in the arterial and venous lines averaged over the time the bolus of the indicator material (or medium) is passing through the sensors and where $S_A$ and $S_V$ are the corresponding dilution areas before and after the hemofilter/organ (FIG. 21).

Figure 22:
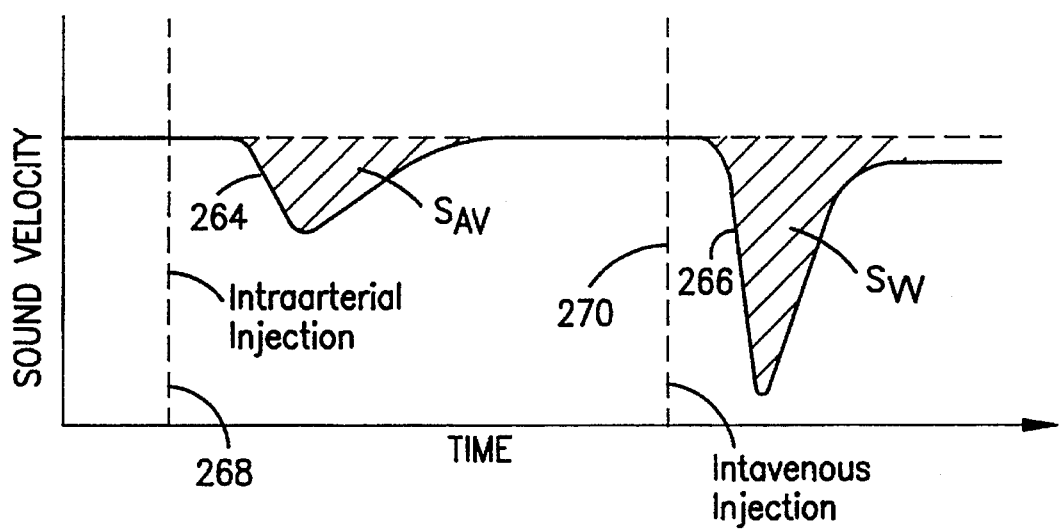
FIG. 22 is a graphical illustration of changes in sound velocity in the arterial and venous lines of a blood treatment system for use in determining blood clearance with an arterial and a venous injection.

In the case where there is only a single sound velocity sensor located on the venous line in any of the systems of FIGS. 1, 10, and 11, the clearance $K_{clear}$ can be calculated by two injections of an indicator material, one before the filter/organ; for example, by way of inlet port 232 in FIG. 11, and the other after the filter/organ; for example, by way of inlet port 236 in FIG. 11. The resulting curves 264 and 266 are illustrated in FIG. 22, where the intraarterial injection at inlet port 232 is made at the time indicated by dotted line 268 to produce the dilution area $S_{AV}$ measured at the venous sound velocity sensor 180'. FIG. 22 also illustrates the later intravenous injection made at inlet port 236 at a time indicated by dotted line 270, which produces the dilution curve 266 and the resulting area $S_{vv}$. The intravenous injection is made at inlet port 236 and is detected at sound velocity sensor 180'. The value $K_{clear}$ can be calculated as follows:

$$K_{clear.} = 1 - S_{AV}/S_{VV} \qquad (Eq. 20)$$

where $S_{AV}$ and $S_{VV}$ are the corresponding dilution areas from the injections before and after the filter/organ.

Figure 23:
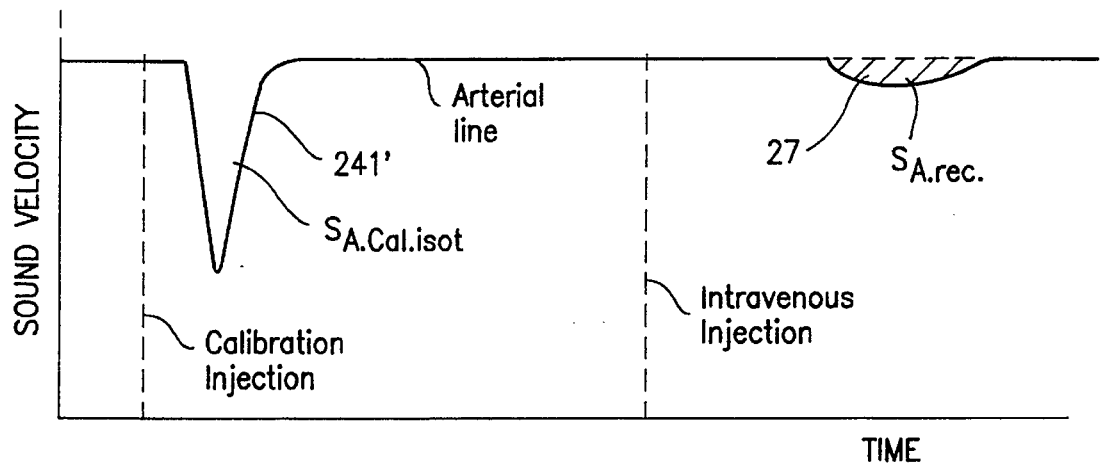
FIG. 23 is a graphical illustration of changes in sound velocity in the arterial and venous lines of a blood treatment system for use in determining blood circulation, using arterial and venous injections.

As noted above, some of the blood returned to the vascular system 152 from the hemodialysis filter in the system of FIG. 11 is recirculated back to the arterial line 150, as indicated at 246. The recirculation coefficient $K_{rec.}$ for such a system can be calculated using intravenous and intraarterial injections of isotonic indicator material at the temperature of the blood flowing in the system, and can be calculated as follows:

$$K_{rec.} = \frac{V_{A.cal.isot.} \cdot S_{A.rec.} \cdot Q_{A.rec.}}{V_{V.isot.} \cdot S_{A.cal.isot.} \cdot Q_{A.cal.}} \qquad (Eq. 21)$$

where $S_{A.rec.}$ is the recirculation dilution area under curve 272, and where $Q_{A.rec.}$ is the blood flow in arterial line 150 during the recirculation, as illustrated in FIG. 23.

Figure 24:
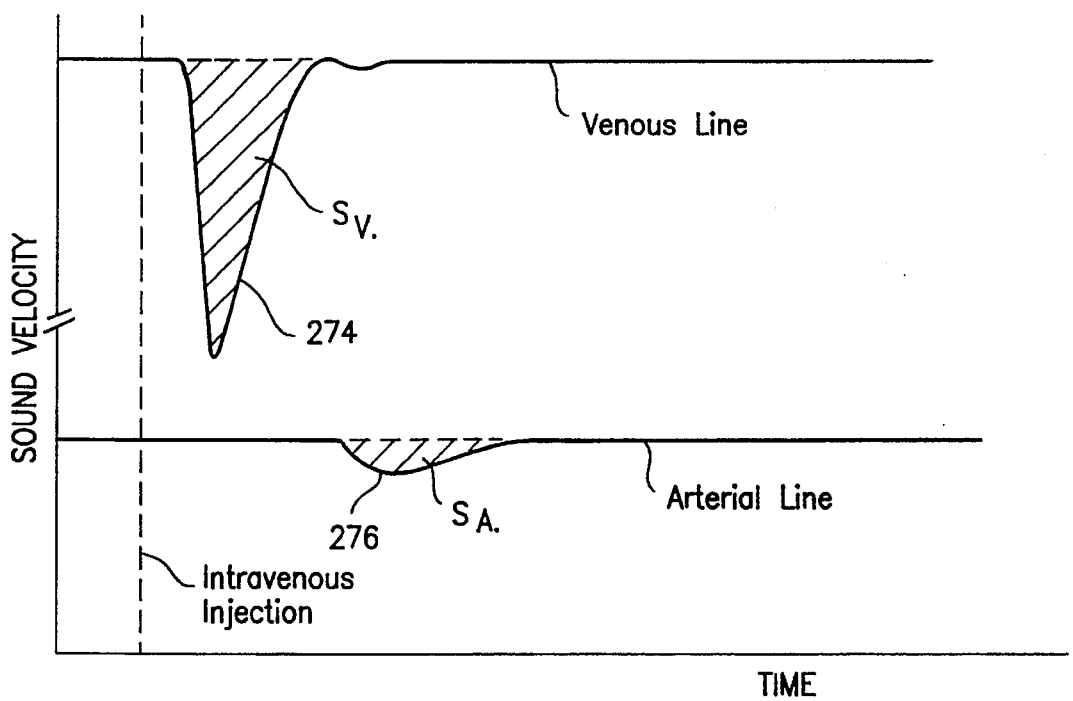
FIG. 24 is a graphical illustration of changes in sound velocity in the arterial and venous lines of a blood treatment system for use in determining blood recirculation, using only an intravenous injection.

When two sensors are used, one located in the arterial and one in the venous tubing lines; for example, sensors 180 and 180' in FIG. 11, only one intravenous injection at port 236 (for FIG. 11) is needed, allowing the recirculation coefficient to be determined as follows:

$$K_{rec.} = \frac{S_A}{S_V} \qquad (Eq. 22)$$

where $S_A$ and $S_V$ represent the dilution areas beneath the curves obtained from the measurements in the arterial line 150 by sensor 180 and within the venous line 158 by sensor 180. These are indicated in FIG. 24 by curves 274 and 276, respectively. It is noted that when the systems of FIGS. 1 and 10 are used, the dilution curves are recorded both before and after organ deconvolution analyses are done.

Figure 25:
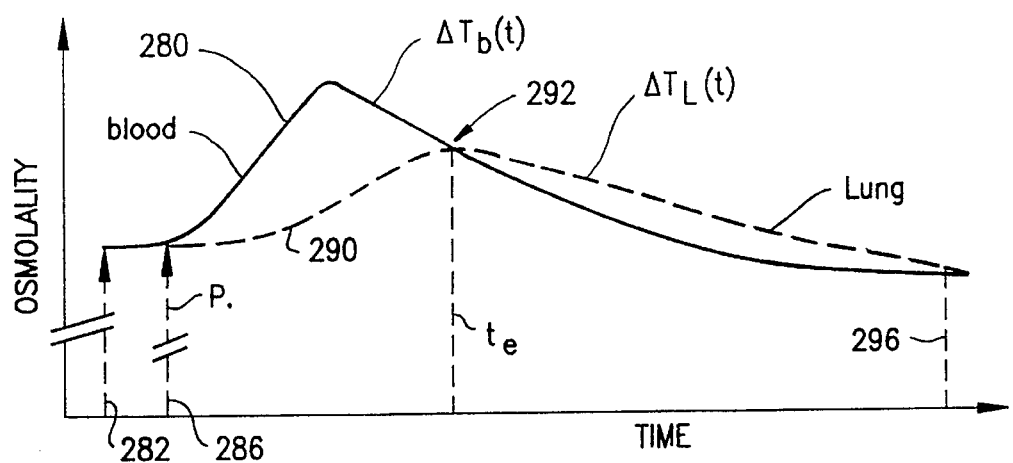
FIGS. 25–27 are graphical illustrations of the transfer of water and solute between a patient's lungs and bloodstream as a bolus of hypertonic solution passes through the lungs.
Figure 26:
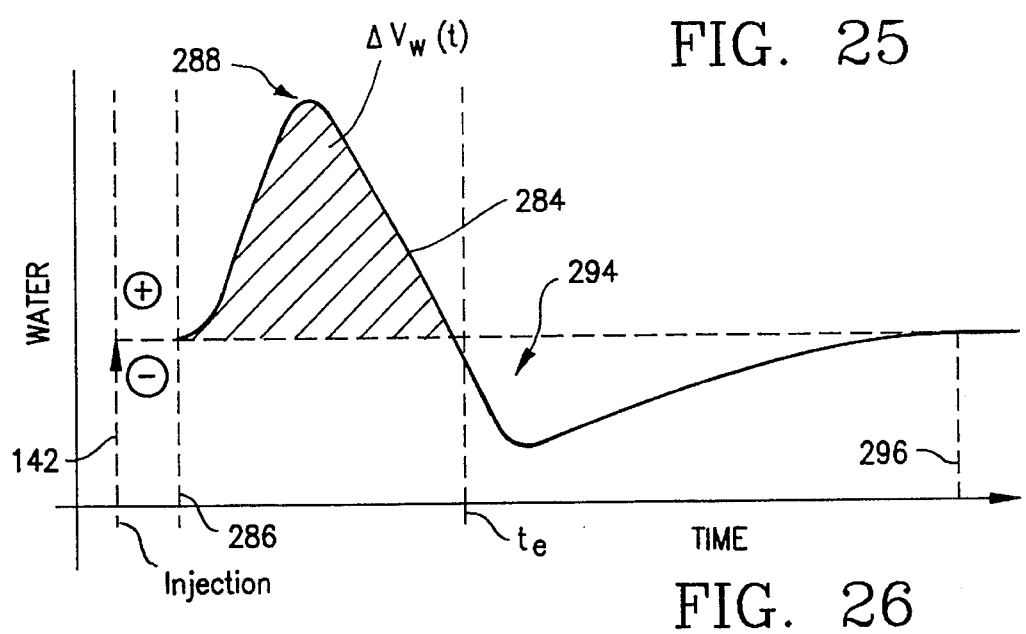
Figure 27:
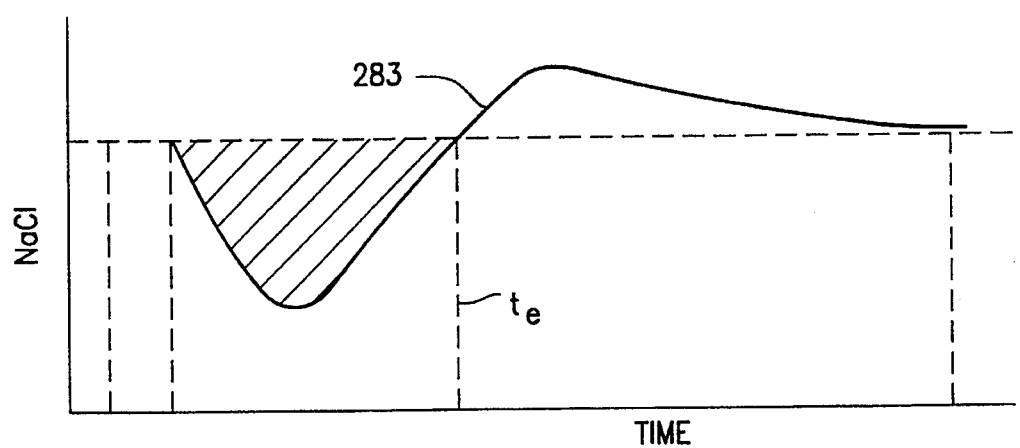

The system of the present invention may also be used to measure extravascular lung water. The osmotically active part of extravascular lung water $V_1$ can be measured from the water volume and the hypertonic solutes moving between the lungs and the vascular system when a bolus of hypertonic indicator solution passes through the vasculature of the lung (N. M. Krivitski, V. V. Kislukhin, "Determination of the Volume of Extravascular Fluid in the Lungs by Blood Electrical Resistance Using a Dilution Method", Med. Tekn. January–February; (1), pp. 6–9 (1987); N. M. Krivitski et al, "Determination of the Volume of Extravascular Fluid in the Lungs by Electroimpedance Indicators", Fisiol. Zh SSSR, April, 75(4), pp. 589–595 (1989). This lung water is expressed by the following equation:

$$V_1 = V_w(t_e) \cdot T_b / \Delta T_b(t_e) \qquad (Eq. 23)$$

where $V_w(t_e)$ is the volume of water transferred to the blood from the lung until time $t_e$ (see FIGS. 25–27); $t_e$ is the time when the osmotic gradient between lung tissue and blood becomes zero (see FIG. 26); $T_b$ is the osmolality of blood before the injection of an indicator; and $\Delta T_b(t_e)$ is the blood osmolality increase at time $t_e$ (see FIG. 25). The change of osmolality is indicated by curve 280 in FIG. 25 following the injection of an indicator at time 282. For the case where a hypertonic solution (for example NaCl), illustrated by curve 283 in FIG. 27, also moves from blood to lungs, then equation 23 will be expressed as follows:

$$V_1 = V_w[(t_e) + G_{NaCl}(t_e)/I] \cdot T_b / \Delta T_b(t_e) \qquad (Eq. 24)$$

where $G_{NaCl}(t_e)$ is the amount of NaCl transferred to the lungs from the blood until $t_e$, and where I is the average concentration of ion plasma and erythrocytes.

Eq. 24 is based on the following considerations. As a hypertonic bolus passes through the lung vasculature, water initially moves from the lung tissue into the blood and NaCl moves from the blood into lung tissue down its osmotic gradient, as illustrated by curve 284 in FIG. 26. As the bolus reaches the lungs at time 286, the curve 284 starts to move in the+direction toward a peak 288. This water movement increases the osmolality of the lung fluids, as indicated by curve 290 in FIG. 25 and after the peak 280 is reached (curve 280 in FIG. 25) gradually decreases the osmolality of the blood. As the bolus moves out of the lung vasculature, the water transfer decreases, as indicated by curve 284 after peak 288, so that at a time t e the osmolality of the lung tissue becomes equal to that of the blood, as indicated at point 292 in FIG. 25, and net water movement ceases. After time $t_e$ the osmolality of the blood falls further, and the osmotic gradient then drives water from the blood into the lung tissue, as indicated at region 294 of curve 284, and drives NaCl from the lung tissue to the blood until osmotic equilibrium is reached at time 296.

The osmolality of blood before injection, $T_b$, and the ion concentration I can be measured routinely. The two values are close, if indicated in the same units. Then, to calculate the extravascular lung water from Eq. 24 it is necessary to determine $V_w(t_e)$, $G_{NaCl}(t_e)$, and $T_b(t_e)$. This can be done utilizing the apparatus of FIGS. 1, 10 and 11 when two dilution sensors are located in the arterial line. For example, in addition to the sound velocity measurement sensor 180 and its detector 184, a second dilution measurement sensor 190 is used. This may, for example, be an electrical impedance sensor with a corresponding electrical impedance detector 194. These sensors are used simultaneously with the blood flow measurement probe utilizing sensor 160 and detector 164, also in the arterial part of the system of FIG. 11.

Lung water can then be measured by injecting a volume $V_{A.inj.cal.isot.}$ of isotonic saline solution at body temperature at a time 298 into the arterial port 232 for calibration. The ultrasound, dilution calibration area $S_{A.cal.isot.sound}$ under curve 300 in FIG. 28 and the electrical impedance dilution area $S_{A.cal.isot.imp.}$ under curve 302 in FIG. 29 are obtained from recording the outputs 302, an intraarterial isotonic injection of a volume $V_{A.inj.cal.hyp.}$ is of detectors 184 and 194, respectively. To obtain curves 300 and made into the arterial port at the time indicated by dotted line 298 and the resulting changes in the arterial line of the blood sound velocity represented by curve 300 in FIG. 28 and the electrical impedance represented by curve 302 in FIG. 29 are recorded. An intravenous injection of isotonic indicator having a volume $V_{v.inj.isot.}$ is then made into port 236 at time 304 to produce dilution curves 306 and 308 and to corresponding dilution areas $S_{A.isot.sound}(t_e)$ and $S_{A.isot.imp}(t_e)$ illustrated in FIGS. 28 and 29.

Thereafter, a volume $V_{A.inj.cal.hyp.}$ of hypertonic saline solution having an os molality $T_{inj.osm.}$ at body temperature is injected at time 309 (FIGS. 30 and 31) into the arterial port 232 for further calibration of the system. A resulting ultrasound dilution calibration area $S_{A.cal.hyp.sound}$, illustrated at curve 310 in FIG. 30, and an electrical impedance solution calibration area $S_{A.cal.hyp.imp.}$ illustrated at 312 in FIG. 31 are then recorded. An intravenous injection of volume $V_{v.inj.hyp.}$ and having the same concentration as the volume $V_{A.inj.cal.hyp.}$ is made into the venous port 236 and the changes in the arterial line of the blood sound velocity $C_{A.hyp.}(t)$ represented by curve 314 in FIG. 30 and the impedance of the hypertonic solution $Z_{A.hyp.}(t)$ illustrated by curve 316 in FIG. 31 are recorded.

During the time a hypertonic solution passes through the lungs, water moves from the lungs to the blood and NaCl leaves the blood and travels to the lungs, as described above. This decreases the blood sound velocity as illustrated in FIG. 30 by the curve 314 and as illustrated by the corresponding area $S_{A.trans.sound}(t_e)$ represented by the cross-hatched area 320. This area 320 is the difference between the total area $S_{A.hyp.sound}(t_e)$ under the dilution curve 314 less the area $S_{A.Or.hyp.sound}(t_e)$, illustrated by cross-hatched area 322, which is the area generated by the dilution of the blood, produced by the indicator solution, which would occur if no osmotic movement occurred, as expressed by the following equation:

$$S_{A.trans.sound}(t_e) = S_{A.hyp.sound}(t_e) - S_{A.Or.hyp.sound}(t_e) \quad \text{(Eq. 25)}$$

By analogy, the water moving from the lungs to the blood and the NaCl leaving the blood and moving to the lungs increases the blood electrical impedance, as is illustrated in FIG. 31. In this figure, curve 324 represents the change in measured impedance upon injection of a hypertonic saline solution which would occur if no osmotic movement occurred. The area under this curve is expressed as $S_{A.Or.hyp.imp.}(t_e)$. Curve 316 represents the change in electrical impedance in the $Z_{A.hyp}(t)$ measured as a result of the intravenous injection of hypertonic saline solution, with the area under this curve up to $t_e$ being $S_{A.hyp.imp.}(t_e)$. The difference between the area under curve 324 and the area under curve 316 is indicated in FIG. 31 at area 326, which is expressed as $S_{A.trans.imp.}(t_e)$. The area 326 may also be expressed as follows:

$$S_{A.trans.imp.}(t_e) = S_{A.Or.hyp.imp.}(t_e) - S_{A.hyp.imp.}(t_e) \quad \text{(Eq. 26)}$$

Because both of the areas $S_{A.trans.sound}(t_e)$ and $S_{A.trans.imp.}(t_e)$ are generated by the same volumes of water $V_w(t_e)$ and salt $G_{NaCl}(t_e)$, two equations with two unknowns make it possible to calculate these volumes:

$$S_{A.hyp.sound}(t_e) - \frac{S_{A.cal.hyp.sound}}{S_{A.cal.isot.sound}} S_{A.isot.sound}(t_c) = \quad \text{(Eq. 27a)}$$
$$K_{W.sound} V_W(t_e) + K_{NaClsound} G_{NaCl}(t_e)$$

$$\frac{S_{A.cal.hyp.imp.}}{S_{A.cal.isot.imp.}} S_{A.isot.imp.}(t_e) - S_{A.hyp.imp.}(t_e) = \quad \text{(Eq. 27b)}$$
$$K_{W.imp.} V_W(t_e) + K_{NaClimp.} G_{NaCl}(t_e)$$

where $K_{W.sound}$ is the sound velocity dilution area from 1 ml of water, $K_{NaCl.sound}$ is the sound velocity dilution area from 1 gram of NaCl, $K_{W.imp.}$ is the electrical impedance dilution area from 1 ml of water, and $K_{NaCl\,imp.}$ is the electrical impedance dilution area from 1 gram of NaCl. These coefficients are calculated from two pairs of equations, as follows:

$$\frac{S_{A.cal.isot.sound}}{V_{A.inj.cal.isot.}} = K_{W.sound} - K_{NaClsound} C_{isot.} \quad \text{(Eq. 28a)}$$

$$\frac{S_{A.cal.hyp.sound}}{V_{A.inj.cal.hyp.}} = K_{W.sound} - K_{NaClsound} C_{hyp.} \quad \text{(Eq. 28b)}$$

and $$\frac{S_{A.cal.isot.imp.}}{V_{A.inj.cal.isot.}} = -K_{W.imp.} + K_{NaClimp.} C_{isot.} \quad \text{(Eq. 29a)}$$

$$\frac{S_{A.cal.hyp.imp.}}{V_{A.inj.cal.hyp.}} = -K_{W.imp.} + K_{NaClimp.} C_{hyp.} \quad \text{(Eq. 29b)}$$

where $C_{isot.}$ it is the concentration of isotonic NaCl and $C_{hyp.}$ it is the concentration of hypertonic NaCl.

Since changes in the blood electrical impedance $Z_{A.hyp}(t)$ are proportional to the injected salt concentration in the blood, and since that in turn is proportional to changes in osmolality, then the change in osmolality at $t_e$, that is, $\Delta T_b(t_e)$ it is given by:

$$\Delta T_b(t_e) = K_p * Z_{A.hyp.}(t_e) \quad \text{(Eq. 30)}$$

where $K_p$ is an unknown coefficient of proportionality. The coefficient $K_p$ can be evaluated by the summation of changes in osmolality and blood electrical impedance over a selected period such as one minute:

$$\int_0^{1\,min} \Delta T_b(t) dt = K_p * \int_0^{1\,min} Z_{A.hyp.}(t) dt \quad \text{(Eq. 31)}$$

This may be restated as follows:

$$V_{V.inj.hyp.} * (T_{inj.osm.} - T_b)/(CO*(1-P)) = K_p * S_{A.imp.hyp.} \quad \text{(Eq. 32)}$$

where $CO*(1-P)$ is the water content of the cardiac output.

Saline equations 30 and 32 for $\Delta T_b(t_e)$ gives the following result:

$$\Delta T_b(t_e) = \frac{V_{V.inj.hyp.} * (T_{inj.osm.} - T_b) * Z_{A.hyp.}(t_e)}{CO * (1-P) * S_{A.imp.hyp.}} \quad \text{(Eq. 33)}$$

Substituting equation 33 and the calculated volumes of water $V_e(t_e)$ and salt $G_{NaCl}(t_e)$ in equation 24, it becomes possible to derive the osmotically active extravascular lung water and the extravascular lung volume from which the water was transferred; that is, the mostly intracellular lung volume, and to derive the extravascular volume to which the NaCl was transferred, which is mostly interstitial lung volume.

Figure 32:
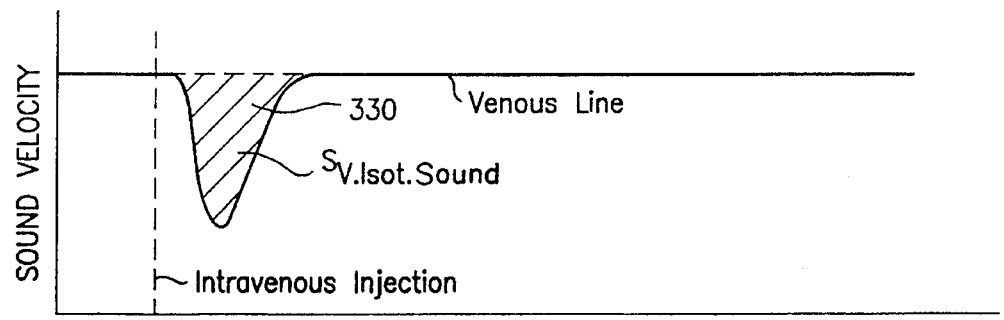
FIGS. 32–35 are graphical illustrations of arterial blood sound velocity and impedance measurements in response to an intravenous injection of isotonic saline solution for lung water volume measurement.
Figure 33:
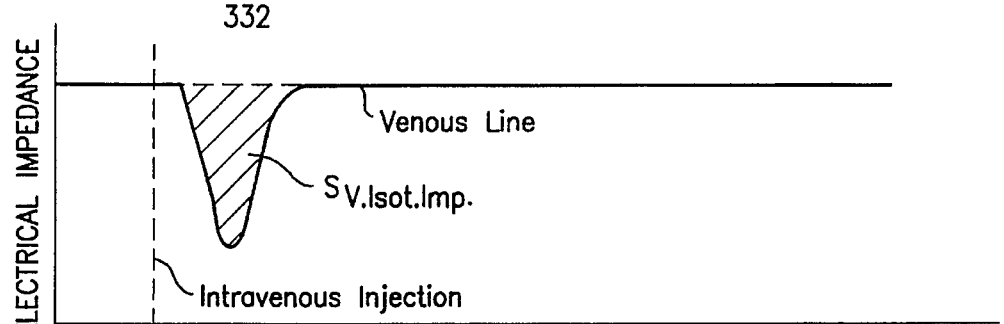
Figure 34:
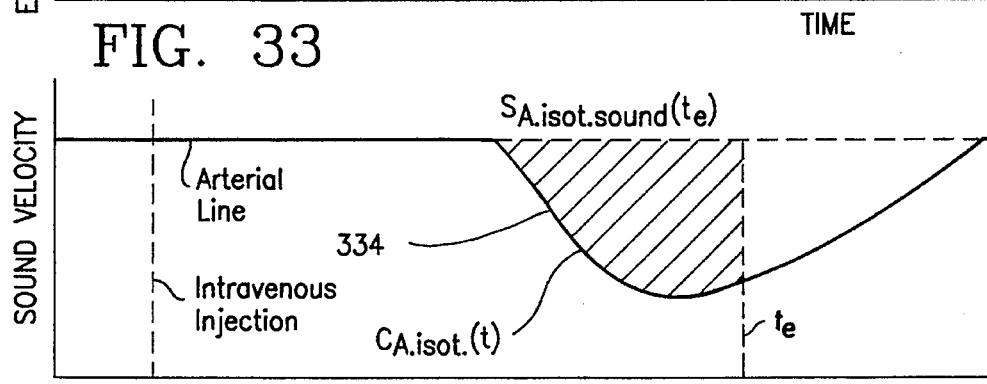
Figure 35:
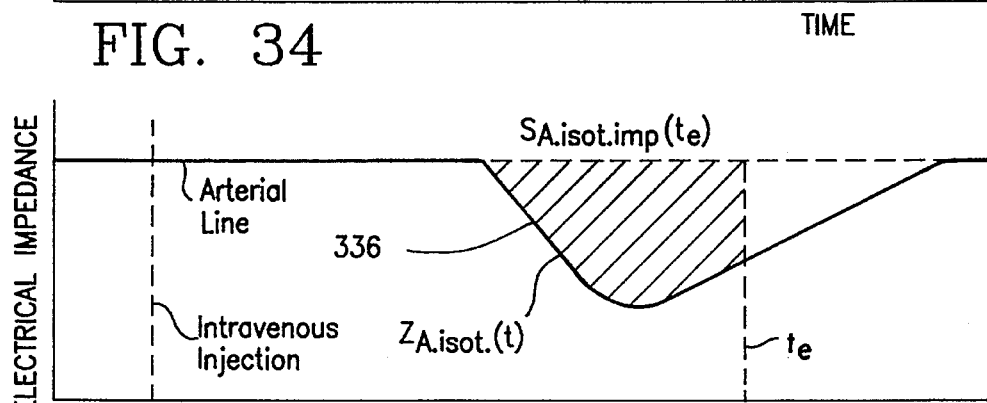
Figure 36:
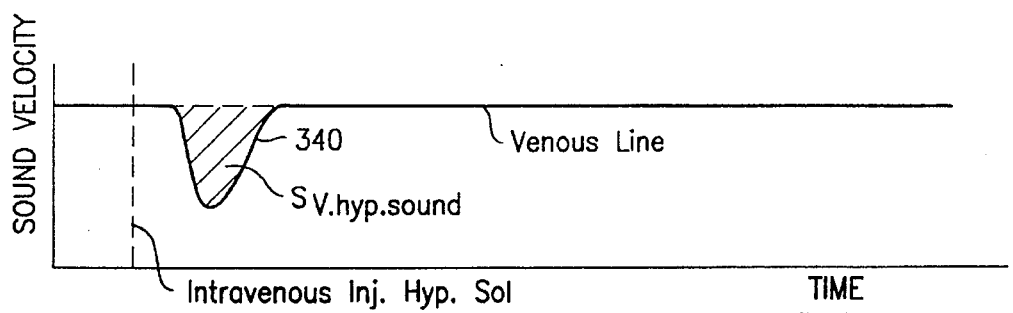
FIGS. 36–39 are graphical illustrations of venous or arterial blood sound velocity dilution and electrical impedance dilution measurements in response to a Venous injection of hypertonic saline solution.
Figure 37:
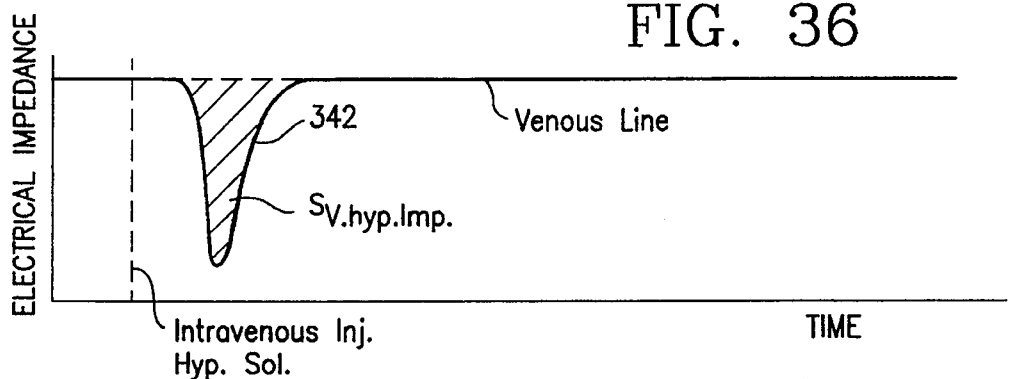

In a system configuration such as that of FIG. 11, where an electrical impedance sensor 190, a sound dilution sensor 180, and a flow probe 160 are present in both the arterial and venous parts of the system, lung water may be measured by injecting a volume $V_{v.inj.isot.}$ of isotonic saline solution at body temperature into the venous port; for example, the port 236. Thereafter, the ultrasound dilution area 330, indicated as $S_{v.isot.sound}$ in FIG. 32 and the electrical impedance dilution area 332, indicated as $S_{v.isot.imp.}$ in FIG. 33, are recorded. In addition, the changes in the arterial line of the blood sound velocity $C_{A.isot}(t)$ illustrated by curve 334 in FIG. 34 and the changes in electrical impedance $Z_{A.isot.}(t)$ illustrated by line 336 in FIG. 35 are also recorded. Thereafter, the $V_{v.inj.hyp.}$ of a hypertonic saline solution having an osmolality $T_{inj.osm.}$ at body temperature is injected into the venous port 236. The resulting ultrasound dilution area $S_{V.hyp.sound}$ is illustrated at curve 340 in FIG. 36 and the corresponding electrical impedance solution area $S_{V.hyp.imp.}$ is illustrated at curve 342 in FIG. 37. Both are in the venous line, and are based on recorded dilution measurements.

Figure 38:
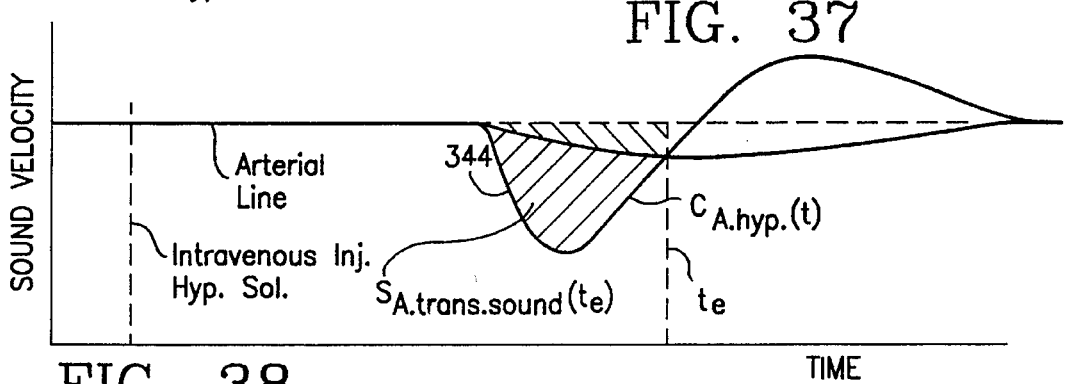
Figure 39:
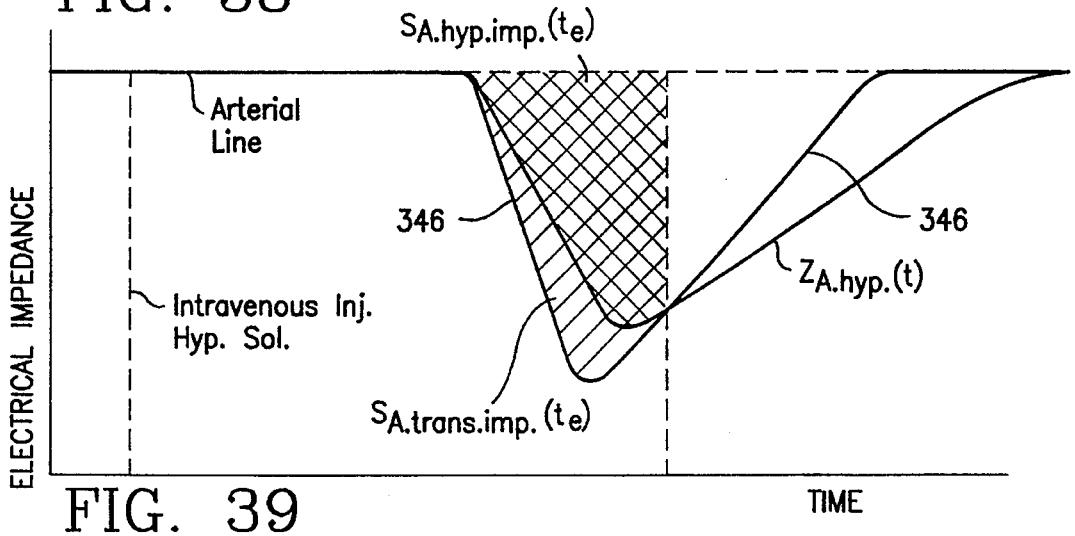

The resulting changes in the arterial line of the blood sound velocity $Z_{A.hyp.}(t)$ illustrated by curve 344 in FIG. 38 and of the arterial line blood impedance $Z_{A.hyp.}(t)$, illustrated by line 346 in FIG. 39 are also recorded. In this embodiment, the same formulas as those described above with respect to equations 25–33 are used by making the following substitutions:

$S_{V.isot.sound}$ for $S_{A.cal.isot.sound}$ $V_{v.isot.}$ for $V_{A.cal.isot.}$ $S_{v.hyp.sound}$ for $S_{A.cal.hyp.sound}$ $V_{v.hyp.}$ for $V_{A.cal.hyp.}$ $S_{v.isot.imp.}$ for $S_{A.cal.isot.imp.}$ $S_{v.hyp.imp.}$ for $S_{A.cal.hyp.imp.}$ to permit a determination of lung water.

Although the foregoing description utilizes a sound velocity measurement in combination with an electrical impedance measurement, it will be understood that the sensors 180 and 190, as well as sensors 180' and 190' can be other types of dilution measurement sensors and detectors. For example, an optical dilution sensor may be combined with a sound dilution sensor or an optical dilution sensor can be combined with an electrical impedance dilution sensor to calculate extravascular lung water in an analogous way. By using a single type of sensor in multiple measurements, relative changes in lung water can be calculated.

Another way to calculate lung water is to inject intravenously a diffusible indicator; for example, cold water, at a temperature other than body temperature, and a non-diffusible indicator such as, for example, a green dye (Oppenheimer et al, "Thermal-dye lung water measurements: effects of edema and embolism", J. Surge. Res. 26; pp. 504–512 (1979)). Extravascular lung water can then be calculated as follows:

$$V_{Therm.} = CO^* (MTT_{Dif.} - MTT_{Nondif.}) \quad \text{(Eq. 34)}$$

where $V_{therm.}$ is the volume of the diffusible and non-diffusible indicators and $MTT_{Dif.} - MTT_{Nondif.}$ represents the mean transit times of the diffusible indicator and the non-diffusible indicator, respectively. The mean transit time is calculated from the following equation, as is known:

$$MTT = \frac{\int F(t)^* t^* dt}{F(t)^* dt} \quad \text{(Eq. 35)}$$

where F(t) is the dilution curve. For this variant of lung water calculation, two sensors are needed, one for the diffusible and one for the non-diffusible indicator.

Figure 40:
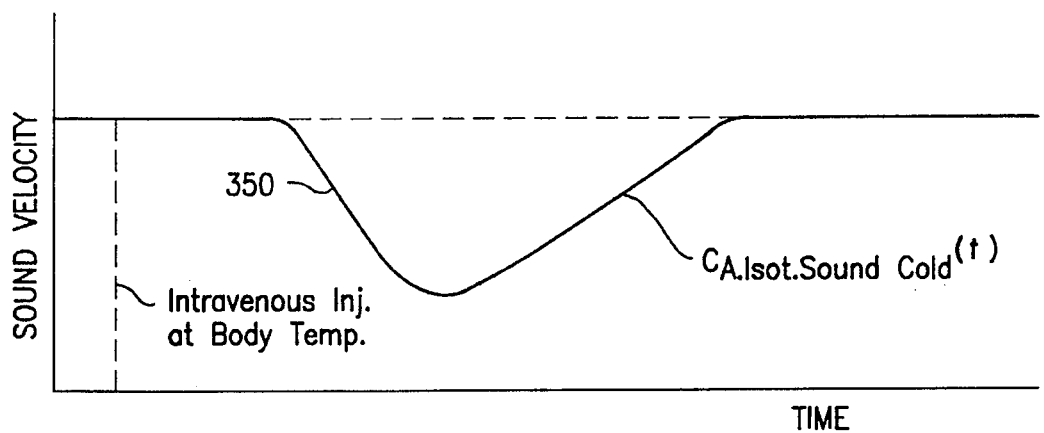
FIGS. 40–42 are graphical illustrations of arterial sound velocity changes due to temperature for lung water measurement.
Figure 41:
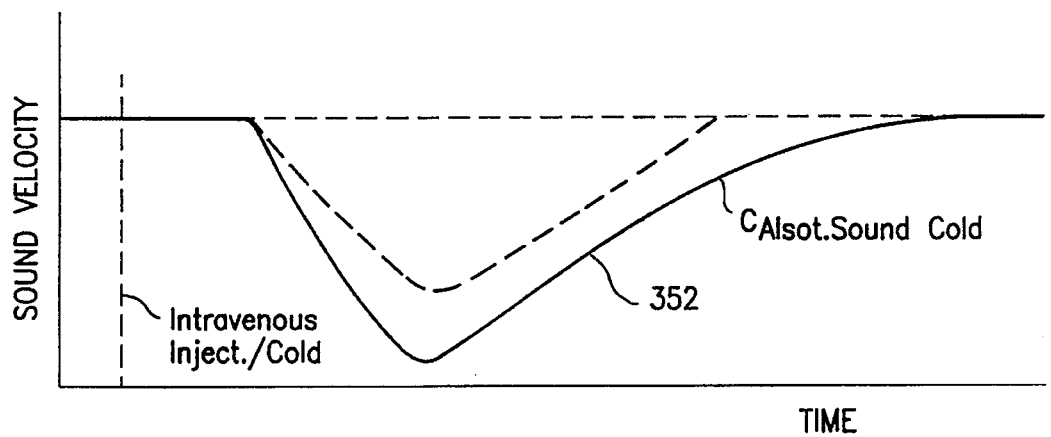
Figure 42:
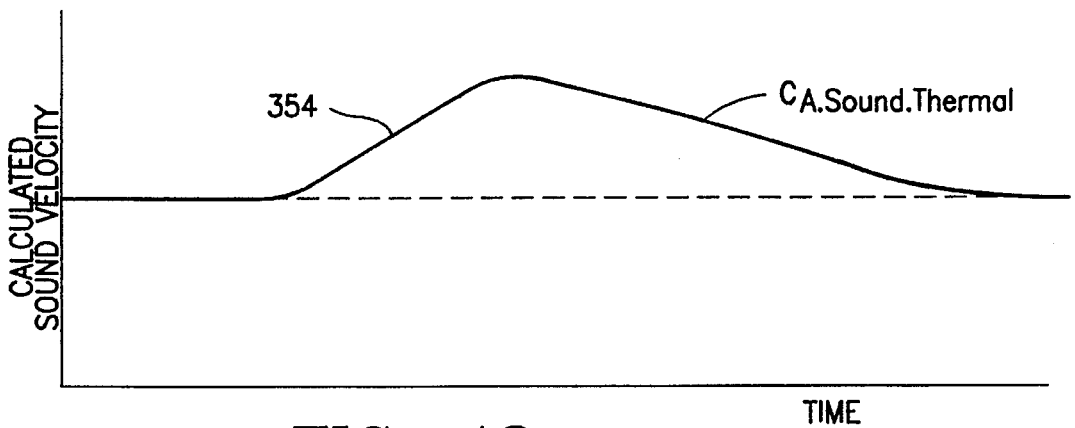

In another embodiment of the invention, lung water can be determined using only a single sound velocity sensor. As indicated in equation 1, blood sound velocity is a function of temperature, and this property is used to record thermal changes caused by blood dilution. Two intravenous isotonic injections of an indicator solution are made, one at body temperature, and the other at a different temperature; for example, colder than body temperature. The sound velocity dilution curve recorded in the arterial line for the intravenous isotonic injection is illustrated by curve 350 in FIG. 40. The sound velocity dilution curve due to the cold injection is illustrated by curve 352 in FIG. 41. The difference between the curve 352 representing the cold injection $C_{A.isot.sound.cold}(t)$ and the sound velocity dilution curve 350 represent ing the body temperature $C_{A.isot.sound}(t)$ gives the sound velocity changes that are related only to temperature changes $C_{A.isot.sound.thermal}(t)$, as indicated in the following equation:

$$C_{A.sound.thetrmal}(t) = C_{A.isot.sound.cold}(t) - C_{A.isot.sound.}(t) \quad \text{(Eq. 36)}$$

Using $C_{A.sound.themal}(t)$ as the curve of the diffusible indicator and $C_{A.isot.sound}(t)$ as the curve of the non-diffusible indicator in the formulas of equations 34 and 35 results in the extravascular lung water volume measured without temperature measurements. In the same way, an electrical impedance sensor may be used to obtain lung water volume.

Although the present invention has been described in terms of preferred embodiments, various modifications may be made without departing from the true spirit and scope thereof, as set forth in the following claims:

What is claimed is:

1. Apparatus for measuring selected parameters of blood, comprising:

a blood circulating system having an arterial portion leading from an upstream blood flow and a venous portion leading to a downstream blood flow, said arterial and venous portions being connected in said circulating system to allow blood to travel from said upstream flow through the circulating system to said downstream flow;

a sound velocity sensor coupled to at least one of said arterial and venous portions for detecting the velocity of blood traveling therein;

an injection port in at least one of said arterial and venous portions;

an indicator injectable through said injection port to produce a bolus in blood flowing in said blood circulating system, said bolus having sound velocity characteristics different from sound velocity characteristics of blood flowing within said system in the absence of said indicator;

a sound velocity detector connected to each said sound velocity sensor for producing an output signal corresponding to sensed sound velocity in blood flowing in said stream to thereby produce sound velocity dilution signals representing changes in blood characteristics due to said bolus; and an evaluating device for determining from said dilution signals selected blood characteristics.

2. A method of measuring hemodynamic parameters by indicator dilution, comprising:

coupling a sound velocity sensor to at least one of an arterial or venous portion of a blood circulating system;

producing a bolus of indicator material in the blood circulating system, said bolus having a sound velocity characteristic which differs from sound velocity characteristics of blood flowing in the blood circulating system to thereby dilute said blood;

detecting, by said sound velocity sensor, changes in sound velocity within said blood caused by dilution of the blood due to said bolus and producing output signals representing changes in blood sound velocity parameters over time caused by said bolus; and evaluating said output signals to determine selected blood characteristics.

3. The method of claim 2, wherein coupling a sound velocity sensor includes positioning the sensor within the arterial or venous portion.

4. The method of claim 2, wherein coupling a sound velocity sensor includes positioning the sensor on an artery or vessel of a patient's blood circulating system.

5. The method of claim 2, wherein coupling a sound velocity sensor includes positioning the sensor on tubing connected between a patient's vascular system and external blood treatment equipment.

6. The method of claim 2, further including generating from said output signals dilution curves representing said changes in blood parameters, and wherein evaluating said output signals includes determining selected blood characteristics from said dilution curves.

7. The method of claim 6, further including coupling a sound amplitude sensor to at least one of said arterial or venous portions of the blood circulating system, detecting, by said sound amplitude sensor, changes in the amplitude of sound waves traveling through blood in said circulating system due to blood dilution caused by said bolus, and evaluating said changes in sound amplitude to determine additional blood characteristics.

8. The method of claim 6, further including detecting, by an impedance sensor, changes in the electrical impedance of blood in said circulating system due to blood dilution caused by said bolus, and evaluating said changes in impedance to determine additional blood characteristics.

9. The method of claim 6, further including detecting, by an optical sensor, changes in the optical density of blood in said circulating system due to blood dilution caused by said bolus, and evaluating said changes in density to determine additional blood characteristics.

10. The method of claim 6, further including detecting, by a thermal sensor, changes in the temperature of blood in said circulating system due to blood dilution caused by said bolus, and evaluating said changes in temperature to determine additional blood characteristics.

11. The method of claim 6, wherein coupling a sound velocity sensor to at least one arterial or venous portion comprises coupling the sound velocity sensor to the venous portion, and wherein the bolus is produced in the arterial portion of said blood circulating system, whereby evaluating said output signals determines solution clearance in said circulating system.

12. The method of claim 6, wherein coupling a sound velocity sensor to at least one arterial or venous portion comprises coupling a corresponding sound velocity sensor to each of said arterial and venous portions to produce respective output signals.

13. The method of claim 12, further including:
coupling a blood dilution sensor to each of said arterial and venous portions;
detecting, by said blood dilution sensors, changes in blood dilution due to said bolus and producing corresponding blood dilution signals; and
evaluating said blood dilution signals with said output signals to determine selected blood characteristics.

14. The method of claim 13, wherein producing a bolus includes injecting into said blood circulating system an indicator fluid and wherein detecting changes in blood dilution includes measuring lung water.

15. A method of measuring a volume of a selected portion of a vascular system, comprising:
injecting into an inlet blood stream flowing into a selected portion of a vascular system a first-quantity of an isotonic solution having a characteristic substantially equal to the same characteristic of said vascular system;
measuring in an outlet blood stream flowing out of said selected portion changes in said blood parameter as said first quantity of said isotonic solution flows through said outlet blood stream to obtain a blood characteristic curve;
injecting into said inlet blood stream a second quantity of said isotonic solution having a characteristic substantially different than that of said blood system;
measuring in said outlet blood stream changes in said blood parameter as said second quantity of said isotonic solution flows through said outlet blood stream;
determining differences in said blood parameter changes to obtain a difference curve; and
comparing said difference curve with said blood characteristic curve to yield a measurement of said volume of said blood system.

16. The method of claim 15, wherein the measuring of a selected blood parameter includes measuring sound velocity in blood in said outlet blood stream; wherein the injecting of a first isotonic solution includes injecting a solution having a temperature substantially the same as that of said blood system; and wherein the injecting of a second isotonic solution includes injecting a solution having a temperature substantially different than that of said blood system to determine the thermal volume of said blood system.

17. The method of claim 15, wherein the measuring of a selected blood parameter includes measuring the electrical impedance of blood in said outlet blood stream; wherein the injecting of a first isotonic solution includes injecting a solution having a temperature substantially the same as that of said blood system; and wherein the injecting of a second isotonic solution includes injecting a solution having a temperature substantially different than that of said blood system to determine the thermal volume of said blood system.

18. The method of claim 15, wherein the measuring of a selected blood parameter includes measuring sound velocity in blood in said outlet blood stream; wherein the injecting of a first isotonic solution includes injecting a solution having an osmolality substantially the same as said blood system; and wherein the injecting of a second isotonic solution includes injecting a solution having an osmolality substantially different than that of said blood system to determine the extravascular volume of a blood system including a selected organ of a patient.

19. The method of claim 15, further including placing a calibrating sensor in an inlet blood stream flowing into said selected portion of said blood system for calibration of said measurements.

20. The method of claim 19, further including injecting calibrating qualities of said isotonic solution in said outlet blood stream prior to said calibrating sensor.

21. The method of claim 15, further including placing a calibrating sensor in said inlet blood stream for calibrating measurements of blood parameters.

22. The method of claim 15, further including measuring a second blood parameter different than the first-named blood parameter, and measuring changes in two blood parameters as each of said first and second quantities of said isotonic solution flow through said outlet blood stream.

23. A method of measuring the extravascular volume of an organ in a patient, comprising injecting a first isotonic solution having a first osmolality into an organ vascular system prior to the organ to dilute blood flowing in said system and passing through said organ;
measuring in said vascular system following said organ changes in the velocity of sound in said blood due to said first solution;
injecting a second isotonic solution having a second osmolality into said system prior to said organ;
measuring in said vascular system following said organ changes in the velocity of sound in said blood due to said second solution; and
comparing said measurements to obtain the extravascular volume of said organ.

24. The method of claim 23, further including calibrating said measurements by further measuring the velocity of sound in said blood in said vascular system prior to said organ.

25. The method of claim 24, further including calibrating said measurements by further injecting a third isotonic solution having said first osmolality and a fourth isotonic solution having said second osmolality in said system after said organ and measuring changes in the velocity of sound in said blood due to said third and fourth solutions.

26. The method of claim 23, wherein said injections and measurements are made prior to and following a patient's lung, respectively, and wherein comparing said measurements provides a measurement of lung water in a patient.

27. A method of measuring blood flow in a patient, comprising:
   injecting, from a catheter placed in the vascular system leading to a selected organ of a patient, a first saline solution at a temperature substantially equal to the patient's body temperature;
   measuring, in the vascular system leading from the selected organ of the patient, changes in the velocity of ultrasound in blood flowing in the vascular system caused by said first solution;
   establishing a curve representing said changes in velocity; and
   determining from an area under said curve the flow of blood from the selected organ.

28. The method of claim 27, including injecting said first saline solution into the vascular system leading to a patient's heart;
   measuring changes in the velocity of ultrasound in blood flowing in an artery leading from the patient's heart; and
   determining cardiac output from said curve.

29. The method of claim 28, further including measuring changes in temperature in said blood flowing in said artery, and correcting said measurement of velocity changes for variations in temperature.

30. A method of measuring total organ blood flow in a patient, comprising:
   injecting a first quantity of an indicator solution in a vascular system downstream of a patient's organ;
   measuring by a first sensor a first selected parameter of said blood flow downstream of said injection and measuring by a second sensor blood flow rate downstream of said injection to measure changes produced by said first indicator solution to calibrate said first sensor;
   injecting a second quantity of said indicator solution upstream of said organ;
   measuring changes in said first selected parameter and changes in blood flow rate produced downstream of said organ by said second quantity of indicator solution; and
   comparing changes produced by said first and second quantities of indicator solution to obtain a measure of total organ blood flow.

31. The method of claim 30, wherein measuring said first parameter comprises measuring the optical density of ultrasound in of blood flowing in said vascular system.

32. The method of claim 30, wherein measuring said first parameter comprises measuring the velocity of ultrasound in blood flowing in said vascular system.

33. The method of claim 32, wherein injecting a first quantity of indicator solution in a vascular system comprises injecting said first quantity in extracorporeal tubing leading from a patient to a blood treatment system, and wherein said measurement of velocity of ultrasound is made in said extracorporeal tubing.

34. The method of claim 33, further including correcting the measurement of ultrasound in said tubing for temperature changes by:
   transmitting ultrasound through said tubing and through said blood and measuring the velocity of said ultrasound;
   simultaneously measuring the amplitude of said ultrasound;
   determining changes in said amplitude due to temperature changes to provide a temperature calibration for said tubing;
   measuring changes in ultrasound velocity produced by said indicator solution; and
   correcting the measured changes in ultrasound velocity due to said indicator solution in accordance with said temperature calibration.

35. Apparatus for measuring blood parameters, comprising:
   a blood system having an upstream end and a downstream end and including an arterial portion and a venous portion connected to carry blood between said upstream and said downstream ends;
   a first sound velocity sensor coupled to said venous portion of said blood system;
   a second sound velocity sensor closely matched to said first sound velocity sensor and coupled to said arterial portion of said blood system;
   an indicator injectable through said injection port to produce an indicator bolus in blood flowing in said system, said indicator bolus having sound velocity characteristics different from sound velocity characteristics of blood flowing within said blood system in the absence of said indicator to thereby dilute said blood sound velocity characteristics; and
   means responsive to said first and second sound velocity sensors for detecting said bolus in said bloodstream and for producing and recording curves representing said diluted sound velocity characteristics.

36. The apparatus of claim 35, further including a blood flow sensor coupled to at least one of said arterial and venous portions of said blood system.

37. The apparatus of claim 35, wherein said means responsive to said first-named sound velocity sensor and said means responsive to said second sound velocity sensor comprise first and second sound velocity detectors; the apparatus further including an evaluating device connected to said detectors for determining selected blood characteristics.

38. The apparatus of claim 37, further including a first dilution sensor coupled to said arterial portion of said blood system and a second dilution sensor coupled to said venous portion of said system, wherein said first and second dilution sensors are electrical impedance sensors.

39. The apparatus of claim 37, further including a first dilution sensor coupled to said arterial portion of said blood system and a second dilution sensor coupled to said venous portion of said system, wherein said first and second dilution sensors are optical sensors.

40. The apparatus of claim 37, further including a catheter in at least one of said arterial and venous portions of said blood system, said catheter incorporating said first-named sound velocity sensor and said injection port for intravascular measurement of blood parameters.

41. The apparatus of claim 40, further including a sound amplitude sensor on said catheter and connected to said evaluating device.

42. The apparatus of claim 41, further including a temperature sensor on said catheter connected to said evaluating device.

43. The apparatus of claim 42, further including an electrical impedance sensor on said catheter connected to said evaluating device.

44. The apparatus of claim 42, further including an optical sensor on said catheter connected to said evaluating device.

45. The apparatus of claim 35, further including a first catheter in said arterial portion of said blood system and a second catheter in said venous portion of said blood system, said first catheter incorporating said injection port and said second catheter incorporating said sound sensor, whereby solution clearance is determinable from said dilution curves.

46. The apparatus of claim 35, wherein said arterial portion and said venous portion of said blood system include corresponding extracorporeal arterial tubing and venous tubing, and wherein said injection port is in said arterial tubing and said first-named sound velocity sensor is coupled to said venous tubing, whereby solution clearance is determinable from said dilution curves.

47. The apparatus of claim 46, further including an evaluating device for determining selected blood characteristics, said apparatus further including blood flow measuring means coupled to said tubing and connected to said evaluating device.

48. The apparatus of claim 46, further including an evaluating device determining selected blood characteristics, said apparatus further including an electrical impedance sensor coupled to said tubing and connected to said evaluating device.

49. The apparatus of claim 46, further including an evaluating device for determining selected blood characteristics, said apparatus further including an optical sensor coupled to said tubing and connected to said evaluating device.

* * * * *